US011696856B2

(12) United States Patent
Erdem et al.

(10) Patent No.: US 11,696,856 B2
(45) Date of Patent: Jul. 11, 2023

(54) THREE-DIMENSIONAL MATERIALS HAVING APERTURES AND VOIDS

(71) Applicant: The Procter & Gamble Company, Cincinnati, OH (US)

(72) Inventors: Gueltekin Erdem, Beijing (CN); Yi Yuan, Beijing (CN)

(73) Assignee: The Procter & Gamble Comoany, Cincinnati, OH (US)

( * ) Notice: Subject to any disclaimer, the term of this patent is extended or adjusted under 35 U.S.C. 154(b) by 975 days.

(21) Appl. No.: 16/551,896

(22) PCT Filed: Mar. 9, 2017

(86) PCT No.: PCT/CN2017/076023
§ 371 (c)(1),
(2) Date: Aug. 27, 2019

(87) PCT Pub. No.: WO2018/161288
PCT Pub. Date: Sep. 13, 2018

(65) Prior Publication Data
US 2020/0179177 A1 Jun. 11, 2020

(51) Int. Cl.
*A61F 13/15* (2006.01)
*A61F 13/512* (2006.01)
(Continued)

(52) U.S. Cl.
CPC ...... *A61F 13/15203* (2013.01); *A61F 13/512* (2013.01); *A61F 13/5116* (2013.01);
(Continued)

(58) Field of Classification Search
CPC .. A61F 13/15; A61F 13/512; A61F 13/51108; A61F 13/5116; A61F 13/5125; A61F 13/5123; B32B 3/24
See application file for complete search history.

(56) References Cited

U.S. PATENT DOCUMENTS

| 4,600,458 A | 7/1986 | Kramer et al. |
| 4,741,941 A | 5/1988 | Englebert et al. |
(Continued)

FOREIGN PATENT DOCUMENTS

| CA | 2518857 A1 | 11/2004 |
| CN | 101090682 A | 12/2007 |
(Continued)

OTHER PUBLICATIONS

International Search Report and Written Opinion, PCT/CN2017/076023 dated Dec. 14, 2017.
(Continued)

*Primary Examiner* — Michele Kidwell
(74) *Attorney, Agent, or Firm* — Amanda Herman Berghauer; Christian M. Best

(57) ABSTRACT

An absorbent article comprising a liquid permeable nonwoven topsheet, a nonwoven second material that is a separate material from the topsheet, a liquid impermeable backsheet, and an absorbent core positioned intermediate the second material and the backsheet. The second material is positioned intermediate the topsheet and absorbent core and is generally planar. The topsheet comprises a plurality of recesses and raised areas, and voids are defined in the raised areas under the topsheet. A first aperture is formed in a substantially central location of the raised areas. The recesses each form a base positioned most distal from the substantially central locations of the raised areas. A second aperture is formed in the bases of the recesses. The first aperture extends through the topsheet, and the second aperture extends through the topsheet and at least partially through the second material.

14 Claims, 19 Drawing Sheets

(51) Int. Cl.

| | |
|---|---|
| *A61F 13/511* | (2006.01) |
| *A61F 13/51* | (2006.01) |
| *A61F 13/537* | (2006.01) |
| *A61F 13/539* | (2006.01) |
| *A61F 13/53* | (2006.01) |

(52) U.S. Cl.
CPC ....... *A61F 13/51104* (2013.01); *A61F 13/539* (2013.01); *A61F 2013/15406* (2013.01); *A61F 2013/51078* (2013.01); *A61F 2013/51178* (2013.01); *A61F 2013/530481* (2013.01); *A61F 2013/53782* (2013.01); *B32B 2555/02* (2013.01)

(56) References Cited

U.S. PATENT DOCUMENTS

| | | | |
|---|---|---|---|
| 4,808,177 A * | 2/1989 | DesMarais | ........ A61F 13/49466 604/385.27 |
| 4,846,821 A | 7/1989 | Lyons | |
| H1575 H | 8/1996 | Daugherty et al. | |
| 6,114,595 A | 9/2000 | Moore et al. | |
| 6,228,462 B1 | 5/2001 | Yee et al. | |
| 7,518,032 B2 | 4/2009 | Seyler | |
| 7,601,415 B2 | 10/2009 | Cree et al. | |
| 8,227,660 B2 | 7/2012 | Hara et al. | |
| 8,637,430 B2 | 1/2014 | Arora et al. | |
| 8,847,002 B2 | 9/2014 | Goh et al. | |
| 9,108,355 B2 | 8/2015 | Kume et al. | |
| 10,206,826 B2 | 2/2019 | Isele et al. | |
| 2003/0191442 A1 | 10/2003 | Bewick-Sonntag et al. | |
| 2004/0140047 A1 | 7/2004 | Sato et al. | |
| 2005/0281976 A1 | 12/2005 | Curro et al. | |
| 2006/0019056 A1 | 1/2006 | Turner et al. | |
| 2006/0286343 A1 | 12/2006 | Curro | |
| 2008/0085399 A1 | 4/2008 | Noda et al. | |
| 2008/0090050 A1 | 4/2008 | Seyler et al. | |
| 2008/0206529 A1 | 8/2008 | Ueminami et al. | |
| 2009/0221979 A1 | 9/2009 | Huang et al. | |
| 2009/0282660 A1 | 11/2009 | Noda et al. | |
| 2010/0035014 A1 | 2/2010 | Hammons et al. | |
| 2010/0209664 A1 | 8/2010 | Sato et al. | |
| 2010/0233438 A1 | 9/2010 | Stone | |
| 2010/0249740 A1 | 9/2010 | Miyamoto et al. | |
| 2010/0310810 A1 | 12/2010 | Bond et al. | |
| 2012/0059343 A1 | 3/2012 | Kume et al. | |
| 2012/0064280 A1 | 3/2012 | Hammons et al. | |
| 2012/0226250 A1 | 9/2012 | Sato et al. | |
| 2012/0238984 A1 | 9/2012 | Paldey | |
| 2013/0261586 A1 | 10/2013 | Lee | |
| 2014/0023822 A1 | 1/2014 | Tai et al. | |
| 2014/0234575 A1 | 8/2014 | Mitsuno et al. | |
| 2015/0059599 A1 | 3/2015 | Boegli | |
| 2015/0182386 A1 | 7/2015 | Nakakado | |
| 2015/0238375 A1 | 8/2015 | Nomoto et al. | |
| 2015/0250660 A1 | 9/2015 | Tally et al. | |
| 2015/0283000 A1 | 10/2015 | Faulks et al. | |
| 2015/0283001 A1 | 10/2015 | Arizti et al. | |
| 2015/0283003 A1 | 10/2015 | Rosati et al. | |
| 2016/0074237 A1 | 3/2016 | Rosati et al. | |
| 2016/0083880 A1 | 3/2016 | Hammons et al. | |
| 2017/0258648 A1 | 9/2017 | Rosati et al. | |
| 2017/0258649 A1 | 9/2017 | Rosati et al. | |
| 2018/0228668 A1 | 8/2018 | Schneider et al. | |

FOREIGN PATENT DOCUMENTS

| | | |
|---|---|---|
| CN | 102138842 A | 8/2011 |
| CN | 201410115950 | 7/2014 |
| CN | 105748209 | 10/2016 |
| CN | 205626299 | 10/2016 |
| EP | 1184075 | 9/2000 |
| EP | 1283028 | 2/2003 |
| EP | 861646 | 5/2003 |
| EP | 1208828 | 7/2005 |
| EP | 1022007 | 3/2006 |
| EP | 1774940 A1 | 4/2007 |
| EP | 1787611 | 5/2007 |
| EP | 2554730 | 2/2013 |
| EP | 1982013 | 6/2013 |
| EP | 2437708 | 9/2013 |
| EP | 2277485 | 5/2014 |
| EP | 1842513 B1 | 9/2014 |
| EP | 2901993 | 9/2016 |
| JP | 02055058 | 8/1988 |
| JP | 5228173 | 5/1993 |
| JP | 2002105835 | 4/2002 |
| JP | 4282428 B2 | 9/2003 |
| JP | 3124190 B2 | 7/2006 |
| JP | 4633698 | 9/2006 |
| JP | 3868880 B2 | 1/2007 |
| JP | 3880502 B2 | 2/2007 |
| JP | 5103100 B2 | 9/2007 |
| JP | 3989218 | 10/2007 |
| JP | 4141124 | 8/2008 |
| JP | 4184253 B2 | 9/2008 |
| JP | 2009153731 | 7/2009 |
| JP | 2009172354 A | 8/2009 |
| JP | 4338327 | 10/2009 |
| JP | 4467405 | 5/2010 |
| JP | 2011200446 A | 10/2011 |
| JP | 2012010884 A | 1/2012 |
| JP | 4901425 B2 | 3/2012 |
| JP | 4931580 B2 | 5/2012 |
| JP | 4974524 B2 | 7/2012 |
| JP | 5011220 | 8/2012 |
| JP | 5074174 B2 | 11/2012 |
| JP | 5099752 B2 | 12/2012 |
| JP | 5148182 B2 | 12/2012 |
| JP | 2013074978 A | 4/2013 |
| JP | 5268416 B2 | 5/2013 |
| JP | 2013126455 A | 6/2013 |
| JP | 5319367 B2 | 7/2013 |
| JP | 2013169388 A | 9/2013 |
| WO | 9301781 A1 | 2/1993 |
| WO | WO9702133 | 1/1997 |
| WO | 9827904 A1 | 7/1998 |
| WO | 200029199 | 5/2000 |
| WO | 200038604 | 7/2000 |
| WO | 200174281 | 10/2001 |
| WO | 200224133 | 3/2002 |
| WO | 03048436 A2 | 6/2003 |
| WO | 200429349 | 4/2004 |
| WO | WO2004058214 | 7/2004 |
| WO | 2004098869 A1 | 11/2004 |
| WO | 2005079542 A2 | 9/2005 |
| WO | 2006007149 A1 | 1/2006 |
| WO | WO2006009997 | 1/2006 |
| WO | 2007001270 A1 | 1/2007 |
| WO | 2007116944 A1 | 10/2007 |
| WO | 2008146594 A1 | 12/2008 |
| WO | 2009139255 A1 | 11/2009 |
| WO | 201074205 | 7/2010 |
| WO | 2010118272 A1 | 10/2010 |
| WO | 2011142272 A1 | 11/2011 |
| WO | WO2012014957 | 2/2012 |
| WO | 2012176656 A1 | 12/2012 |
| WO | WO2013005782 | 1/2013 |
| WO | 201347890 | 4/2013 |
| WO | 201377074 | 5/2013 |
| WO | 2013399463 | 7/2013 |
| WO | WO2013099625 | 7/2013 |
| WO | 2013147222 A1 | 10/2013 |
| WO | 2013175360 A1 | 11/2013 |
| WO | 2014084066 A1 | 6/2014 |
| WO | 201545842 | 4/2015 |
| WO | WO2015143772 | 10/2015 |
| WO | WO2016040096 | 3/2016 |
| WO | WO2016159952 | 10/2016 |

(56) References Cited

FOREIGN PATENT DOCUMENTS

| WO | WO2017002409 | 1/2017 |
|----|--------------|--------|
| WO | WO2017030136 | 2/2017 |

OTHER PUBLICATIONS

Supplemental International Search Report and Written Opinion, PCT/CN2017/076023 dated Apr. 7, 2019.
All Office Actions, U.S. Appl. No. 15/454,008.
All Office Actions, U.S. Appl. No. 15/454,024.

* cited by examiner

THREE-DIMENSIONAL MATERIALS HAVING APERTURES AND VOIDS

CROSS REFERENCE TO RELATED APPLICATION

This application is a national stage entry into the United States and claims priority under 35 U.S.C. § 371 to Chinese PCT Patent Application Serial No. PCT/CN2017/076023, filed on Mar. 9, 2017, the entire disclosure of which is hereby incorporated by reference.

FIELD

The present disclosure is directed to three-dimensional materials having apertures and voids. The present disclosure is also directed to absorbent articles comprising three-dimensional nonwoven materials having apertures and voids.

BACKGROUND

Absorbent articles typically comprise a topsheet, a backsheet, and an absorbent core disposed between the topsheet and the backsheet. The absorbent article may also comprise an acquisition layer that temporarily stores liquid bodily exudates received from the topsheet and an optional distribution layer that transfers and distributes the liquid bodily exudates from the acquisition layer to the absorbent core.

Many absorbent articles, including diapers, rely on capillary action to achieve fluid acquisition and wicking of fluid away from the skin of a wearer. The structure of absorbent articles generally results in a configuration in which there is a higher capillary pressure in the bottom layer and a lower capillary pressure in the top layer. Some absorbent articles also comprise textured and/or apertured topsheets to improve fluid handling properties. However, absorbent articles made from these materials are typically less soft. In addition, the fluid handling properties of these materials may be somewhat limited, particularly when handling both urine and viscous body fluids such as a runny bowel movement ("BM").

Thus, there is a need for improved materials for use in absorbent articles. In particular, a need exists for improved nonwoven materials or laminates of nonwoven materials or laminates comprising nonwoven materials that have improved dryness, and have improved absorbency and retention of BM and other bodily fluids, and reduced run-off. In particular, a need exists for improved nonwoven materials having three-dimensional features with apertures and voids to provide improved absorbency and retention of BM and other bodily fluids, and reduced run-off.

SUMMARY

The present disclosure provides improved three-dimensional multi-layer apertured materials such as nonwoven materials, and absorbent articles comprising the same, having improved absorbency and retention of BM and other bodily fluids and reduced run-off. Absorbent articles may use the three-dimensional multi-layer apertured materials as topsheets, for example. The three-dimensional multi-layer apertured materials may comprise apertures in one or more layers of the multi-layer materials and may create significant void volume for better absorbency, retention, and reduced run-off of BM and other bodily fluids. The apertures may allow BM and other bodily fluids to quickly penetrate into the absorbent articles, while the increased void volumes may allow for better retention of BM or other bodily fluids. Further, the increased void volumes may reduce the spread of BM and other bodily fluids, once captured, thereby providing the benefit of reduced run-off. Additionally, the three-dimensional multi-layer apertured materials of the present disclosure may act to wipe BM or other bodily fluids off of or to wick BM or other bodily fluids away from the skin of a wearer, during wearer movement. The three-dimensional multi-layer apertured materials of the present disclosure may also provide high surface areas and contact with the skin to entangle BM or other bodily fluids and at least reduce BM or other bodily fluids from sticking to the skin.

In accordance with an aspect of the present disclosure, an absorbent article is provided comprising: a liquid permeable nonwoven topsheet; a nonwoven second material that may be a separate material from the topsheet; a liquid impermeable backsheet; and an absorbent core that may be positioned at least partially intermediate the second material and the liquid impermeable backsheet. The second material may be positioned intermediate the liquid permeable topsheet and the absorbent core. The second material may be generally planar. The topsheet may comprise a plurality of recesses and a plurality of raised areas, in which portions of the recesses may be joined to portions of the second material. A void may be defined intermediate a garment-facing surface of the topsheet and a wearer-facing surface of the second material in the raised areas. A first aperture may be formed in a substantially central location of at least a majority of the raised areas. The first aperture may extend through only the topsheet. The recesses may each comprise a base positioned most distal from the substantially central locations of the raised areas. A second aperture may be formed in at least a majority of the bases of the recesses. The second aperture may extend through the topsheet and at least partially through the second material. Sections of the recesses and the raised areas intermediate the first apertures and the second apertures may be free of any apertures.

In accordance with an aspect of the present disclosure, an absorbent article is provided comprising: a liquid permeable nonwoven topsheet; a nonwoven second material that may be a separate material from the topsheet; a liquid impermeable backsheet; and an absorbent core that may be positioned at least partially intermediate the second material and the liquid impermeable backsheet. The second material may be positioned intermediate the liquid permeable topsheet and the absorbent core. The second material may be generally planar. The topsheet may comprise a plurality of recesses and a plurality of raised areas. A void may be defined intermediate a garment-facing surface of the topsheet and a wearer-facing surface of the second material in the raised areas. The recesses may each comprise a base positioned most distal from the raised areas. Portions of the recesses may be joined to portions of the second material. An aperture may be formed in at least a majority of the bases of the recesses. The aperture may extend through the topsheet and at least partially through the second material. The raised areas may be free of apertures. The topsheet or the second material may comprise a hydrophobic cotton-containing layer.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Figure 1:
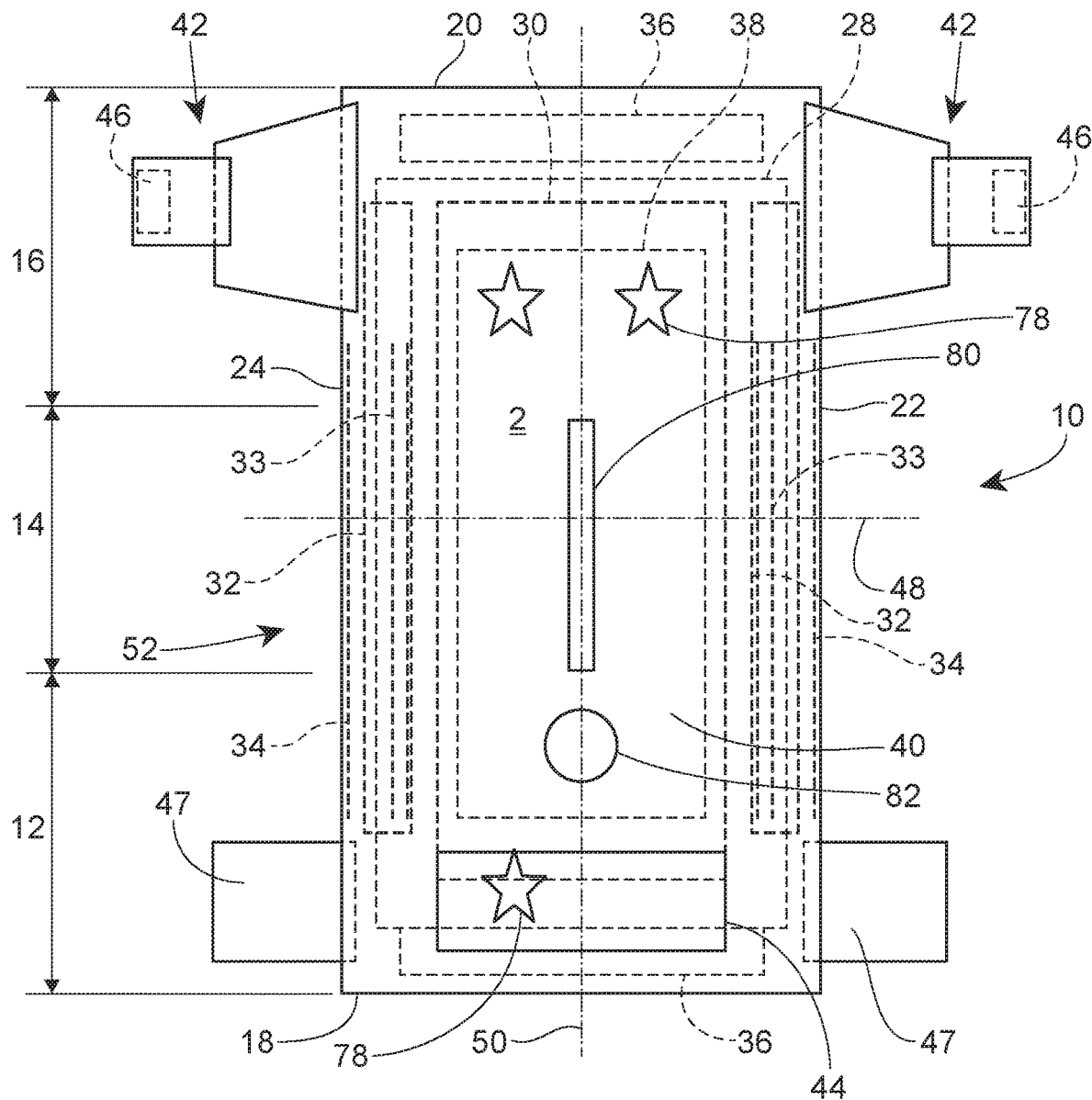
FIG. 1 is a plan view of an example absorbent article in the form of a taped diaper, garment-facing surface facing the viewer, in a flat laid-out state.

Various non-limiting forms of the present disclosure will now be described to provide an overall understanding of the principles of the structure, function, manufacture, and use of the three-dimensional materials having apertures and voids disclosed herein. One or more examples of these non-limiting forms are illustrated in the accompanying drawings. Those of ordinary skill in the art will understand that the three-dimensional materials having apertures and voids described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Definition of Terms

The term "absorbent article" may include disposable articles such as sanitary napkins, panty liners, tampons, interlabial devices, wound dressings, pants, taped diapers, adult incontinence articles, wipes, and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. The nonwoven materials described herein may comprise at least part of other articles such as scouring pads, wet or dry-mop pads (such as SWIFFER® pads), paper towels, toilet tissue, and the like.

The term "aperture", as used herein, refers to a predetermined and intentional hole that extends completely through a web or structure (that is, a through hole). The apertures may either be formed cleanly through the web so that the material surrounding the aperture lies in the same plane as the web prior to the formation of the aperture (a "two dimensional" aperture), or the holes may be formed such that at least some of the material surrounding the opening is pushed out of the plane of the web. In the latter case, the apertures may resemble a depression with an aperture therein, and may be referred to herein as a "three dimensional" aperture, a subset of apertures. The term "aperture" does not refer to unintentional variances in the nonwoven material, unintentional tears formed during manufacturing, or pores in the nonwoven materials.

The term "disposable" may be used herein to describe absorbent articles and other products which are not intended to be laundered or otherwise restored or reused as an absorbent article or product (i.e., they are intended to be discarded after use and, preferably, to be recycled, composted or otherwise disposed of in an environmentally compatible manner).

The term "joined to" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The term "joined to" encompasses configurations in which an element is secured to another element at selected locations, as well as configurations in which an element is completely secured to another element across the entire surface of one of the elements. The term "joined to" includes any known manner in which elements may be secured including, but not limited to mechanical entanglement.

The term "machine direction" or "MD" means the path that material, such as a web, follows through a manufacturing process.

The term "web" is used herein to refer to a material whose primary dimension is X-Y, i.e., along its length (or longitudinal direction) and width (or transverse direction). It should be understood that the term "web" is not necessarily limited to single layers or sheets of material. Thus, the web may comprise laminates or combinations of several sheets of the requisite type of materials.

General Description of an Absorbent Article

Figure 2:
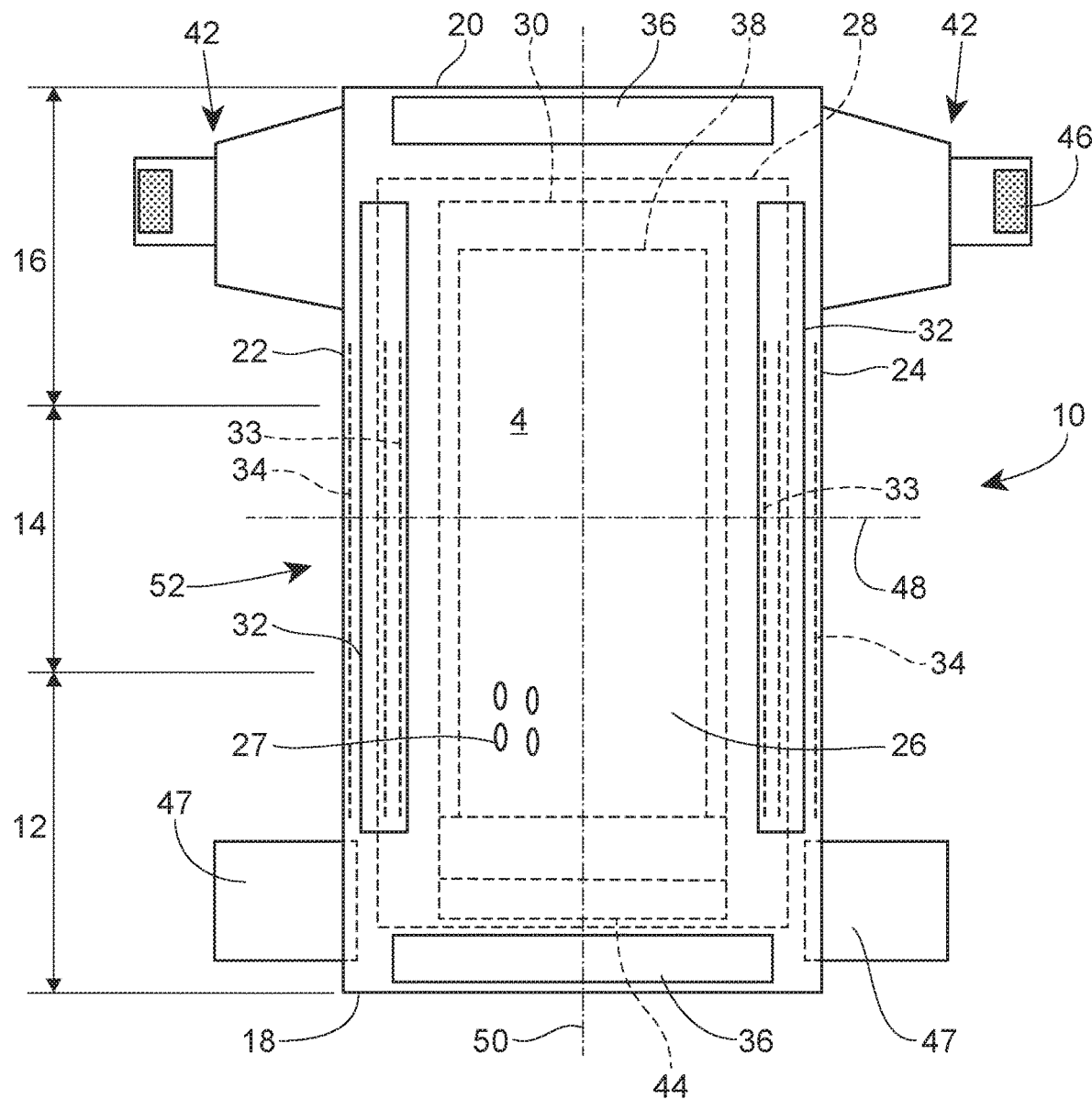
FIG. 2 is a plan view of the example absorbent article of FIG. 1, wearer-facing surface facing the viewer, in a flat laid-out state.
Figure 3:
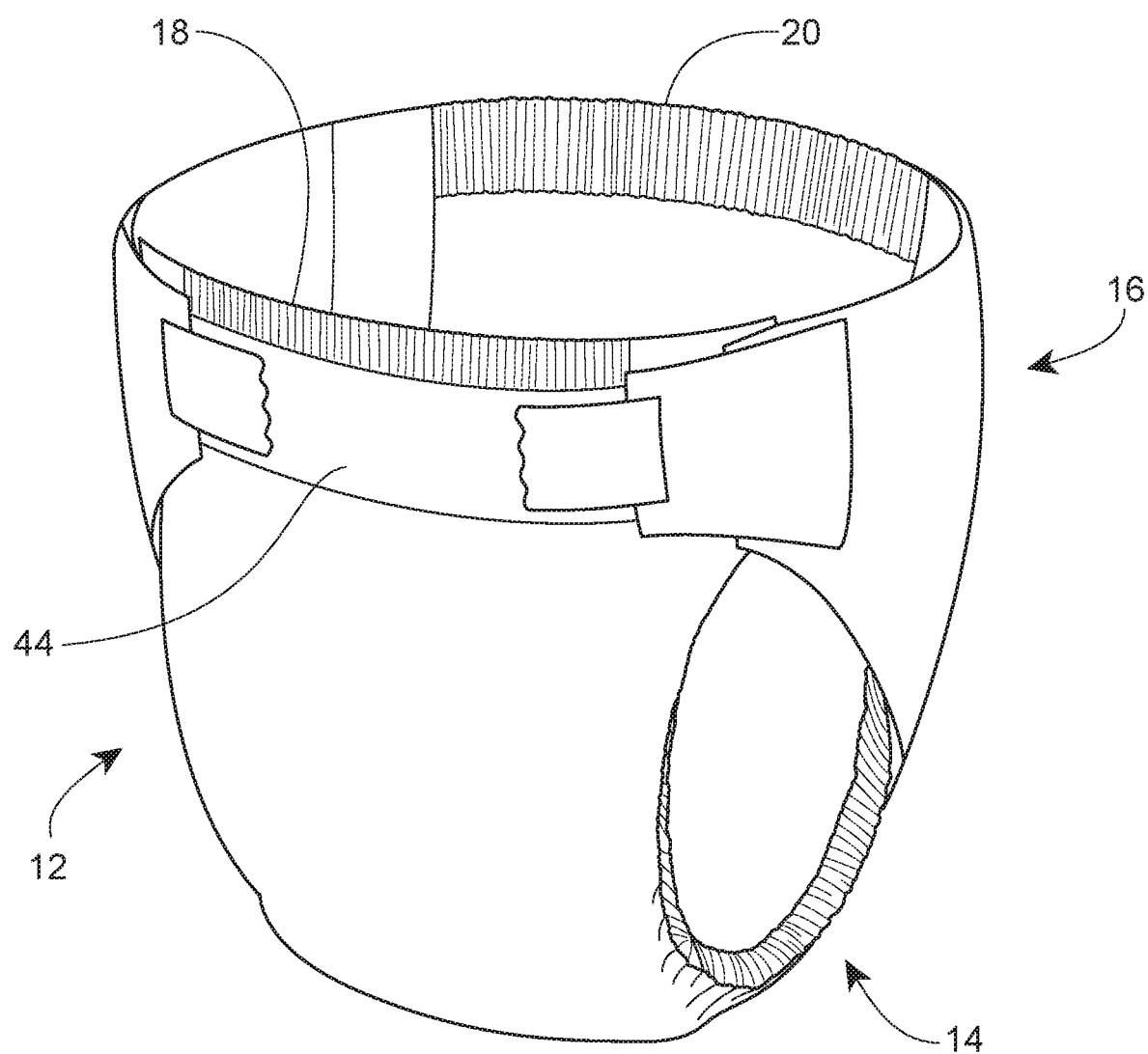
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front waist region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
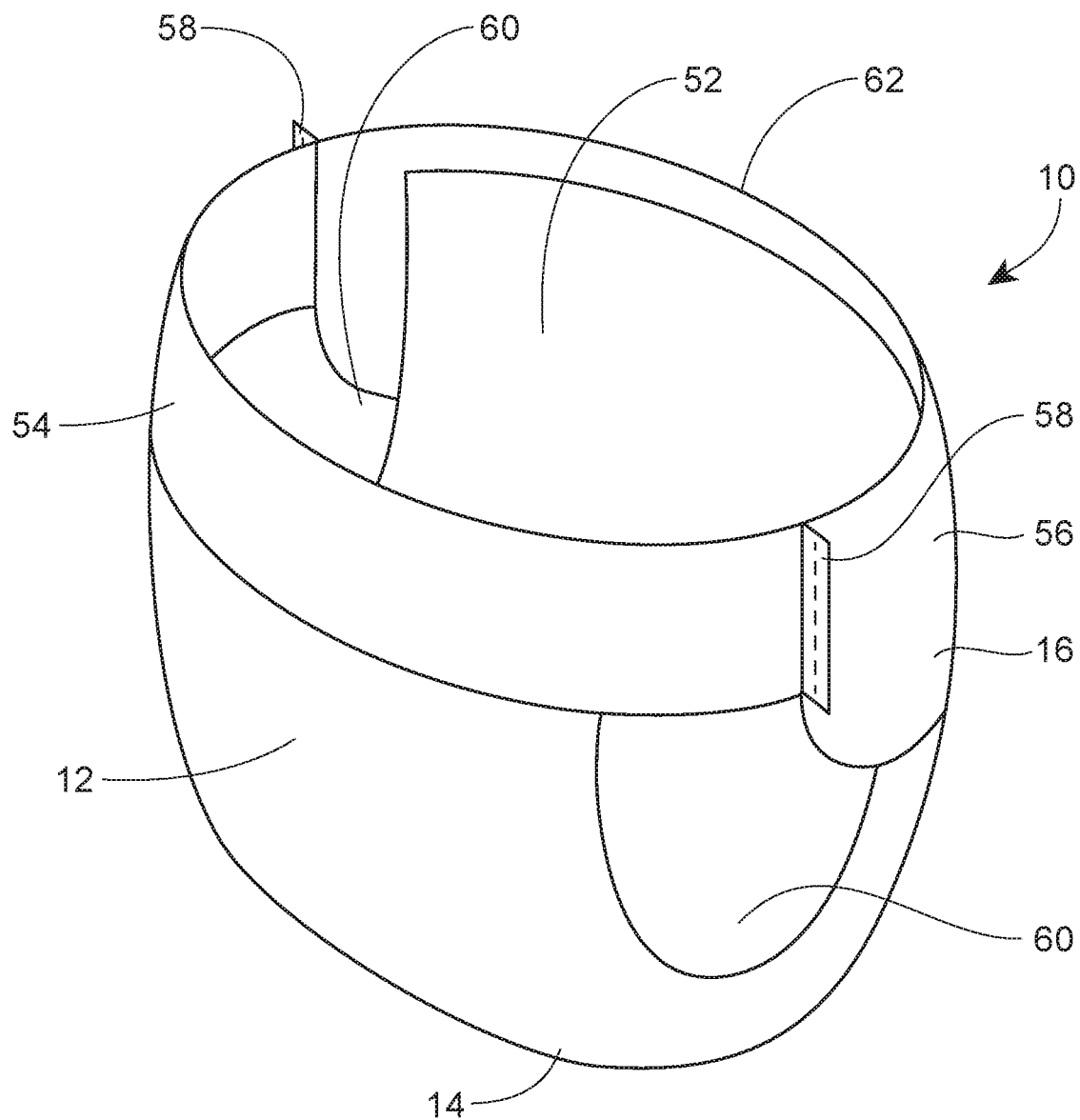
FIG. 4 is a front perspective view of an absorbent article in the form of a pant.
Figure 5:
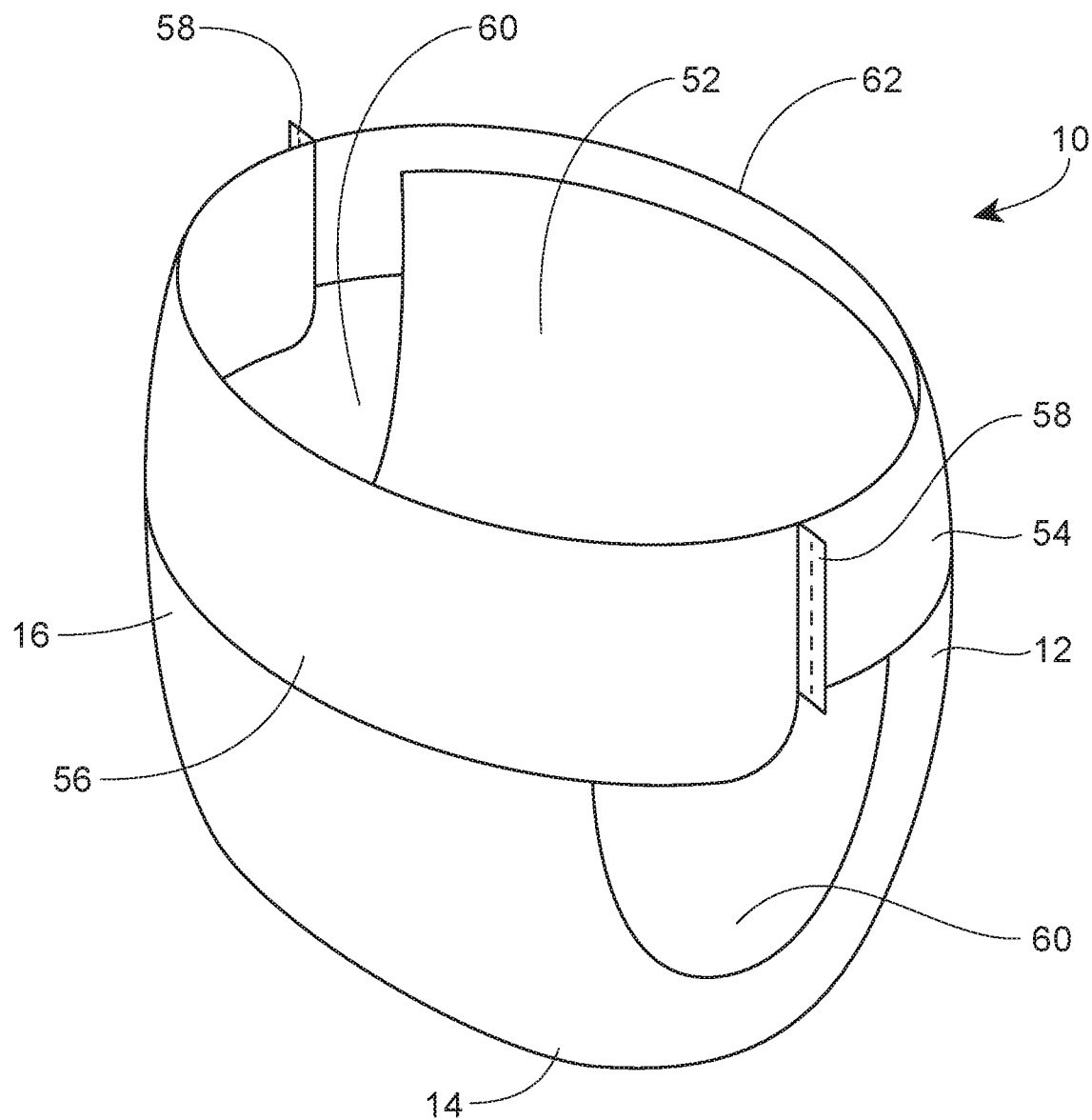
FIG. 5 is a rear perspective view of the absorbent article of FIG. 4.
Figure 6:
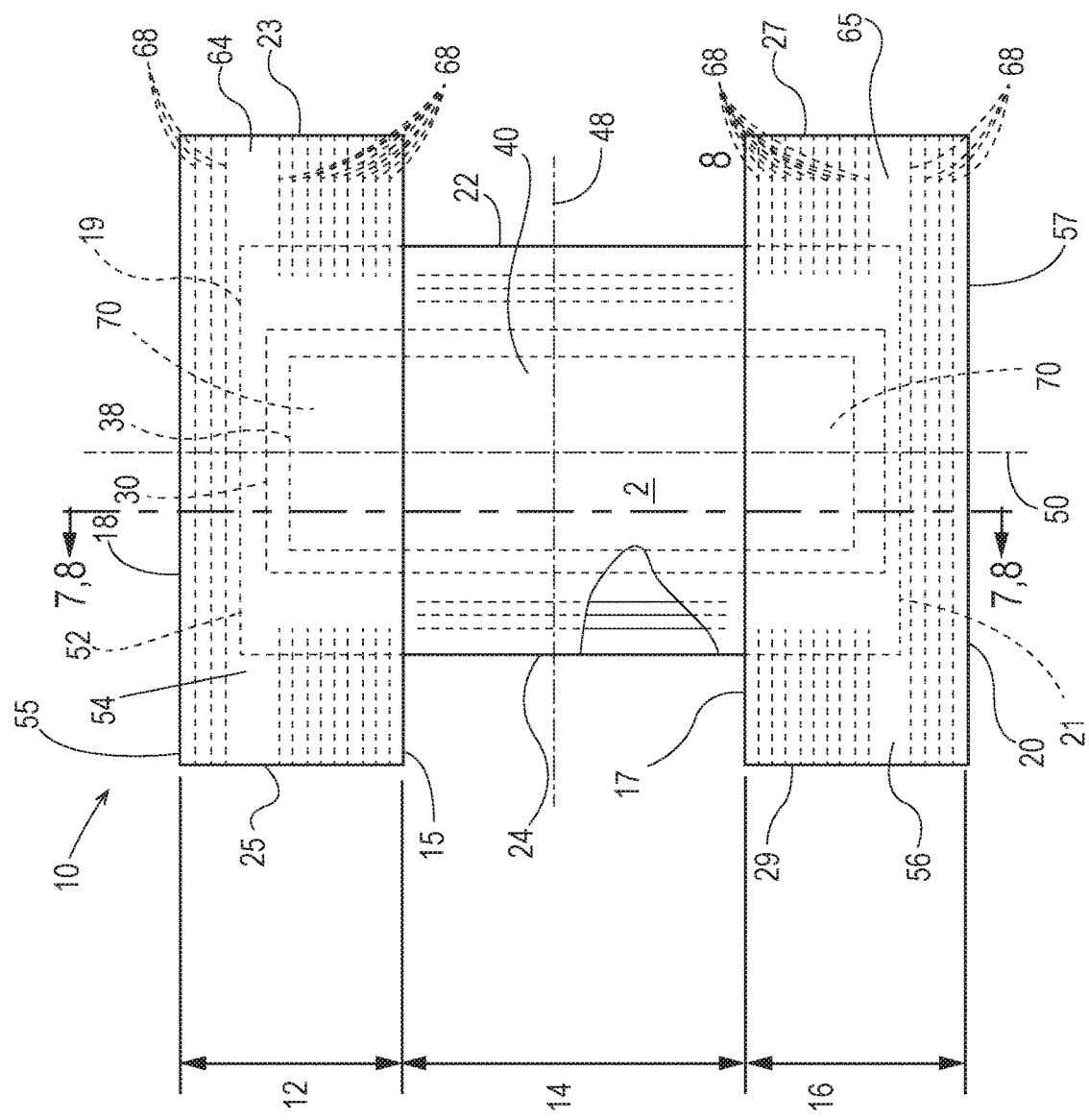
FIG. 6 is a plan view of the absorbent article of FIG. 4, laid flat, with a garment-facing surface facing the viewer.
Figure 7:
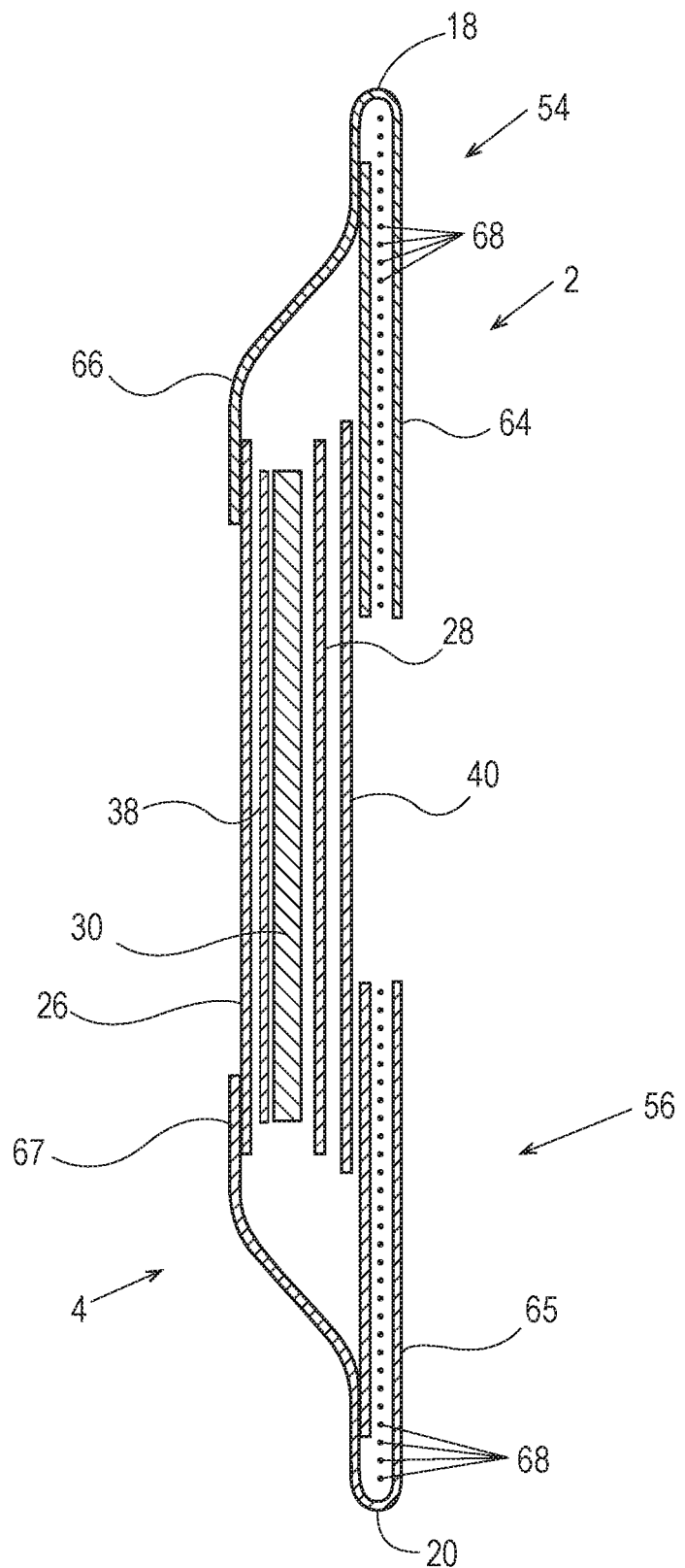
FIG. 7 is a cross-sectional view of the absorbent article taken about line 7-7 of FIG. 6.
Figure 8:
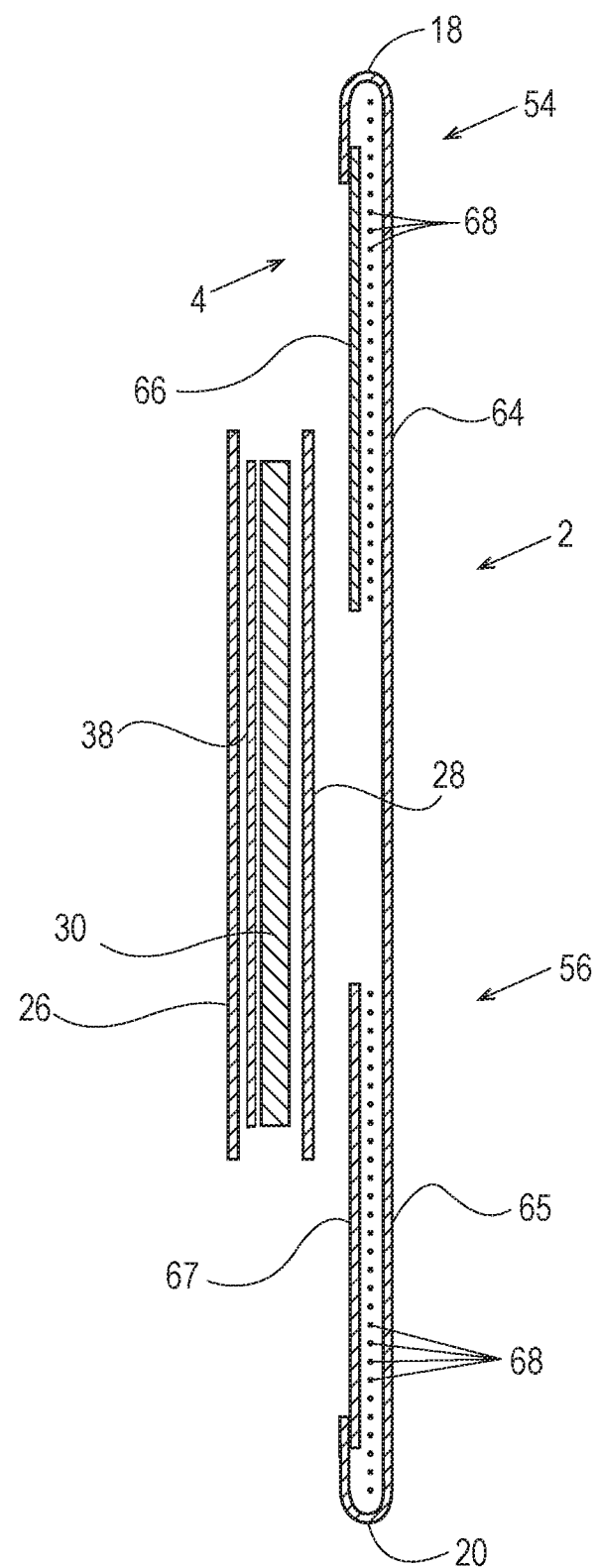
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIG. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIG. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or may, alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 27), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features.

Absorbent Core

Figure 9:
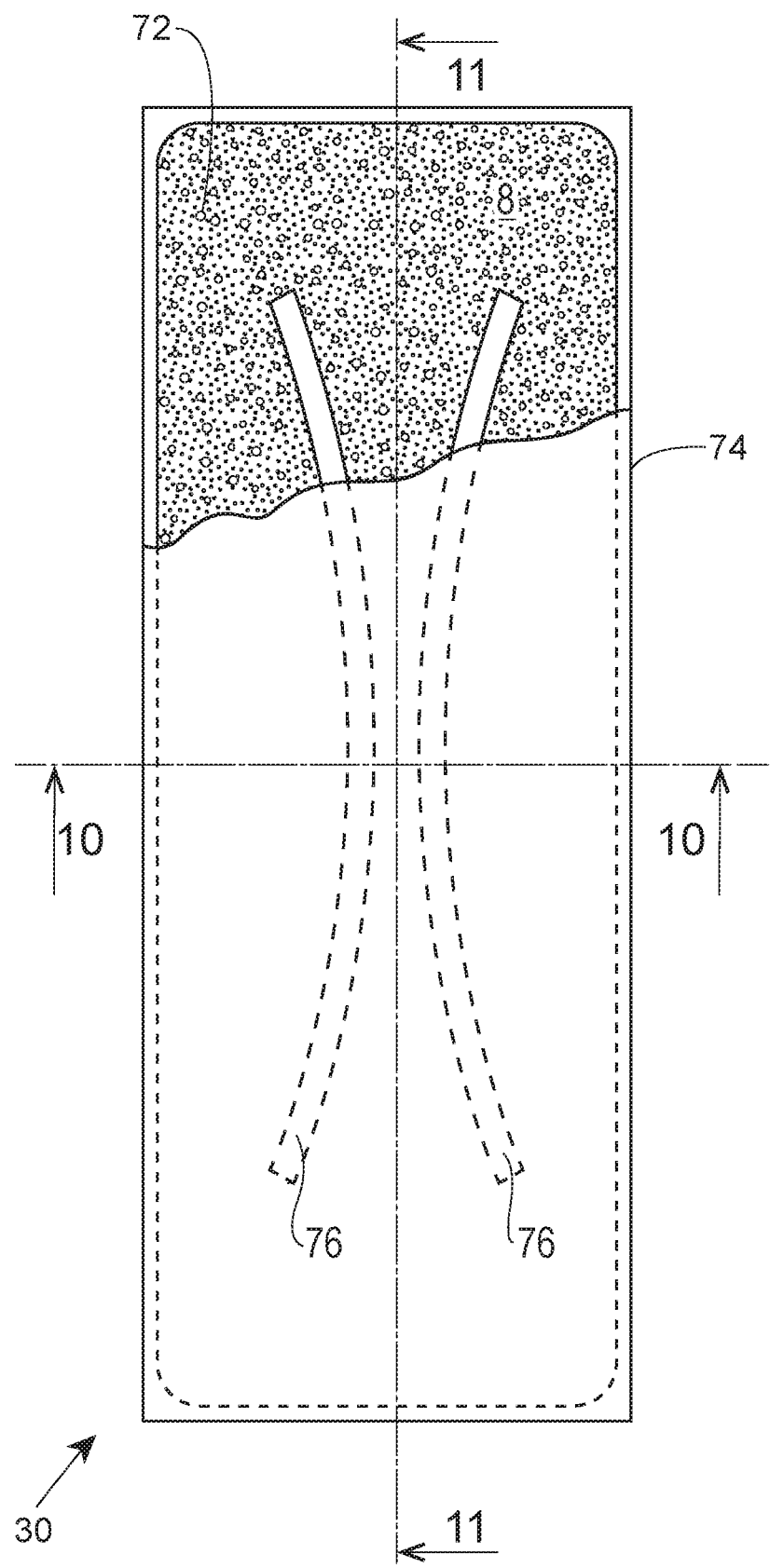
FIG. 9 is a plan view of an example absorbent core or an absorbent article.
Figure 10:
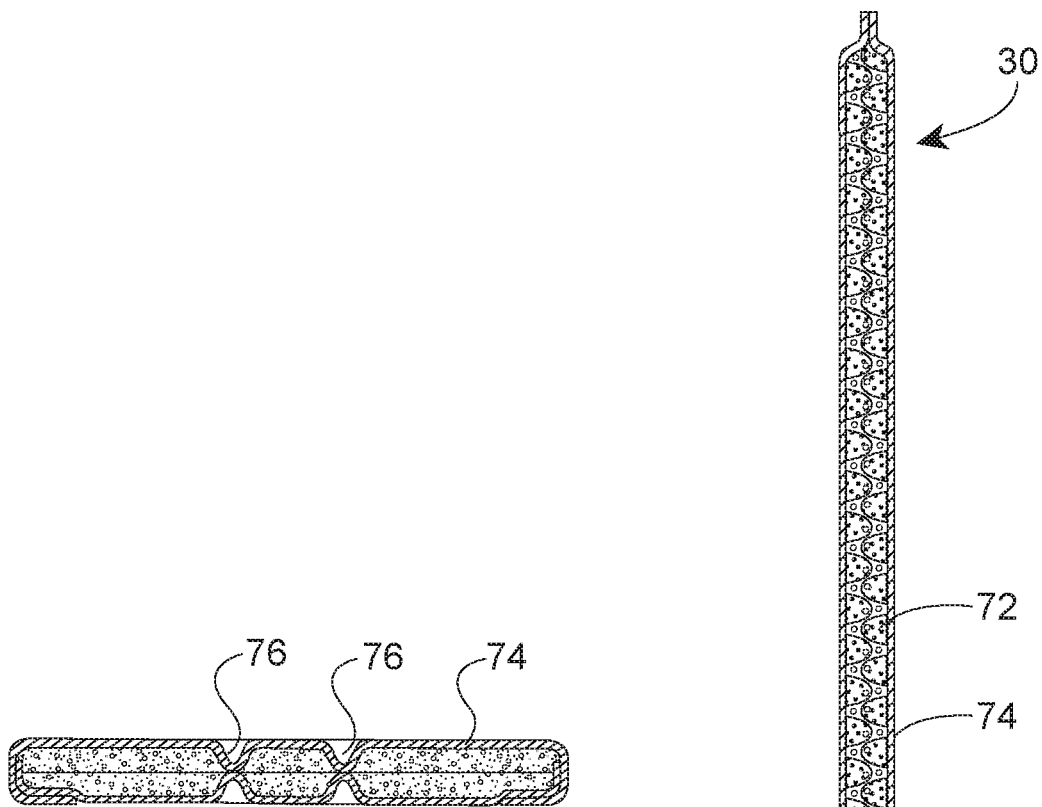
FIG. 10 is a cross-sectional view, taken about line 10-10, of the absorbent core of FIG. 9.
Figure 11:
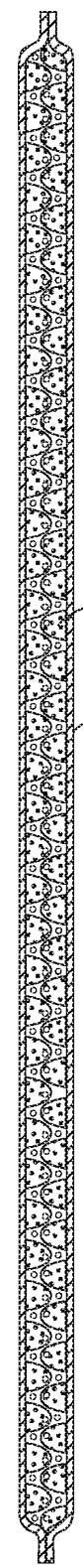
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that providing significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portion of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic stands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Arrays

"Array" means a display of packages comprising disposable absorbent articles of different article constructions (e.g., different elastomeric materials [compositionally and/or structurally] in the side panels, side flaps and/or belts flaps, different graphic elements, different product structures, fasteners or lack thereof). The packages may have the same brand and/or sub-brand and/or the same trademark registration and/or having been manufactured by or for a common manufacturer and the packages may be available at a common point of sale (e.g. oriented in proximity to each other in a given area of a retail store). An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Huggies," and same sub-brand, for example, "Pull-Ups." A different product in the array may have the same brand "Huggies" and the sub-brand "Little Movers." The differences between the "Pull-Ups" product of the array and the "Little Movers" product in the array may include product form, application style, different fastening designs or other structural elements intended to address the differences in physiological or psychological development. Furthermore, the packaging is distinctly different in that "Pull-Ups" is packaged in a predominately blue or pink film bag and "Little Movers" is packaged in a predominately red film bag.

Further regarding "Arrays," as another example an array may be formed by different products having different product forms manufactured by the same manufacturer, for example, "Kimberly-Clark", and bearing a common trademark registration for example, one product may have the brand name "Huggies," and sub-brand, for example, "Pull-Ups." A different product in the array may have a brand/sub-brand "Good Nites" and both are registered trademarks of The Kimberly-Clark Corporation and/or are manufactured by Kimberly-Clark. Arrays also often have the same trademarks, including trademarks of the brand, sub-brand, and/or features and/or benefits across the line-up. "On-line Array" means an "Array" distributed by a common on-line source.

Sanitary Napkin

Figure 12:
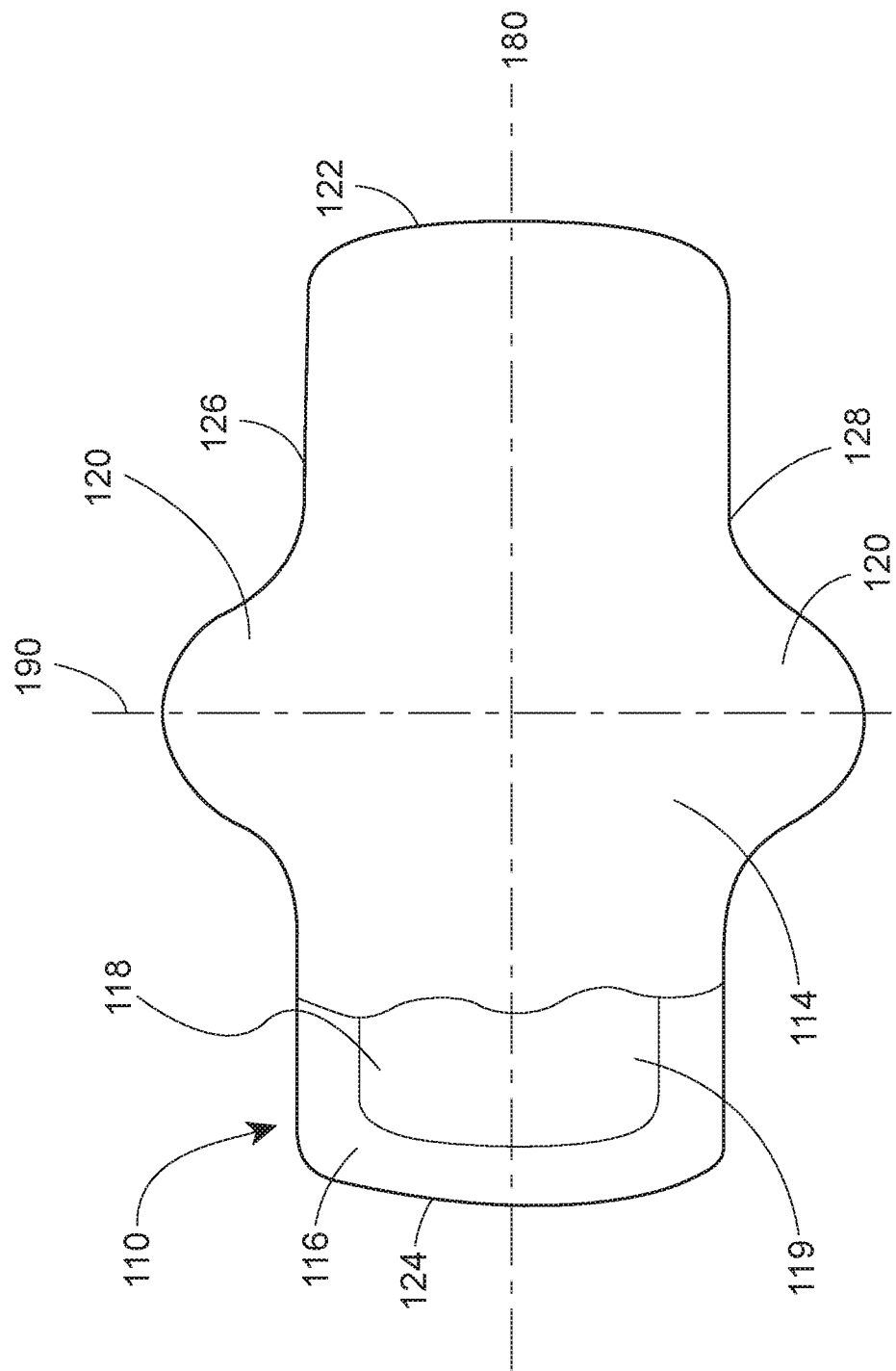
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

Examples Cross-Sections of Absorbent Articles

Figure 13:
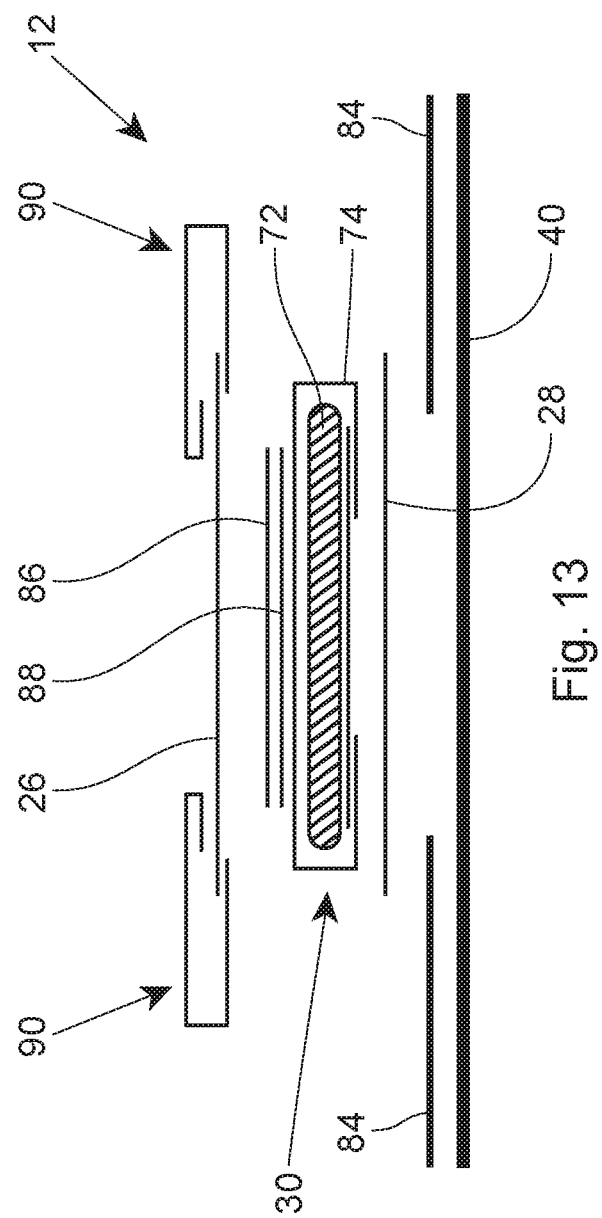
FIG. 13 is an example cross-sectional view taken within a front waist region of an absorbent article.
Figure 14:
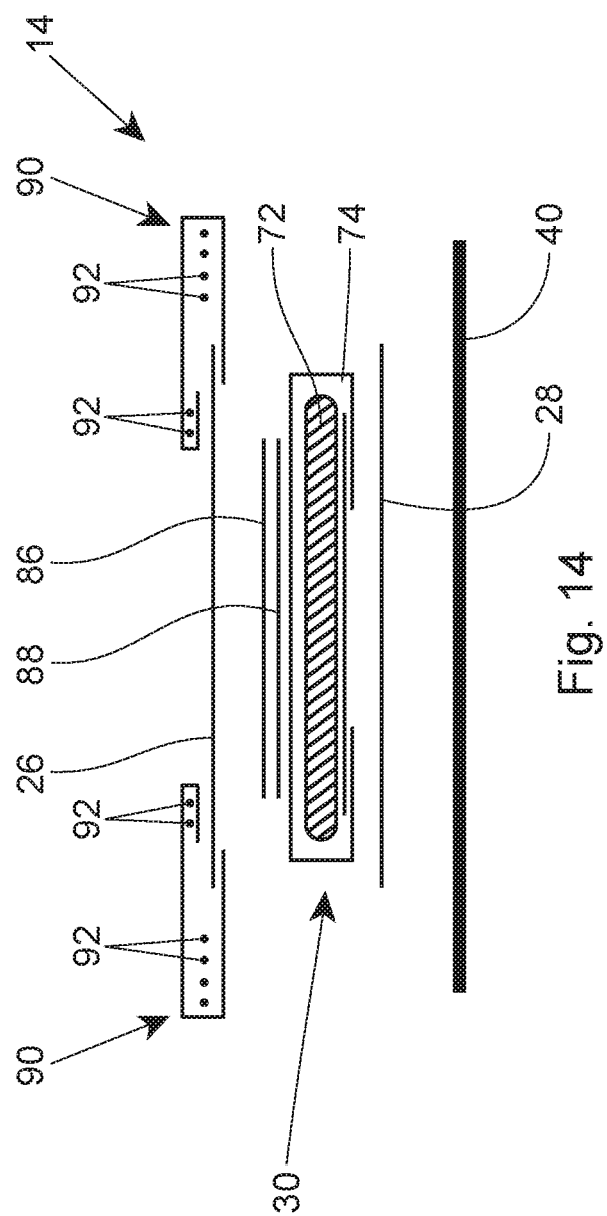
FIG. 14 is an example cross-sectional view taken within a crotch region of an absorbent article.
Figure 15:
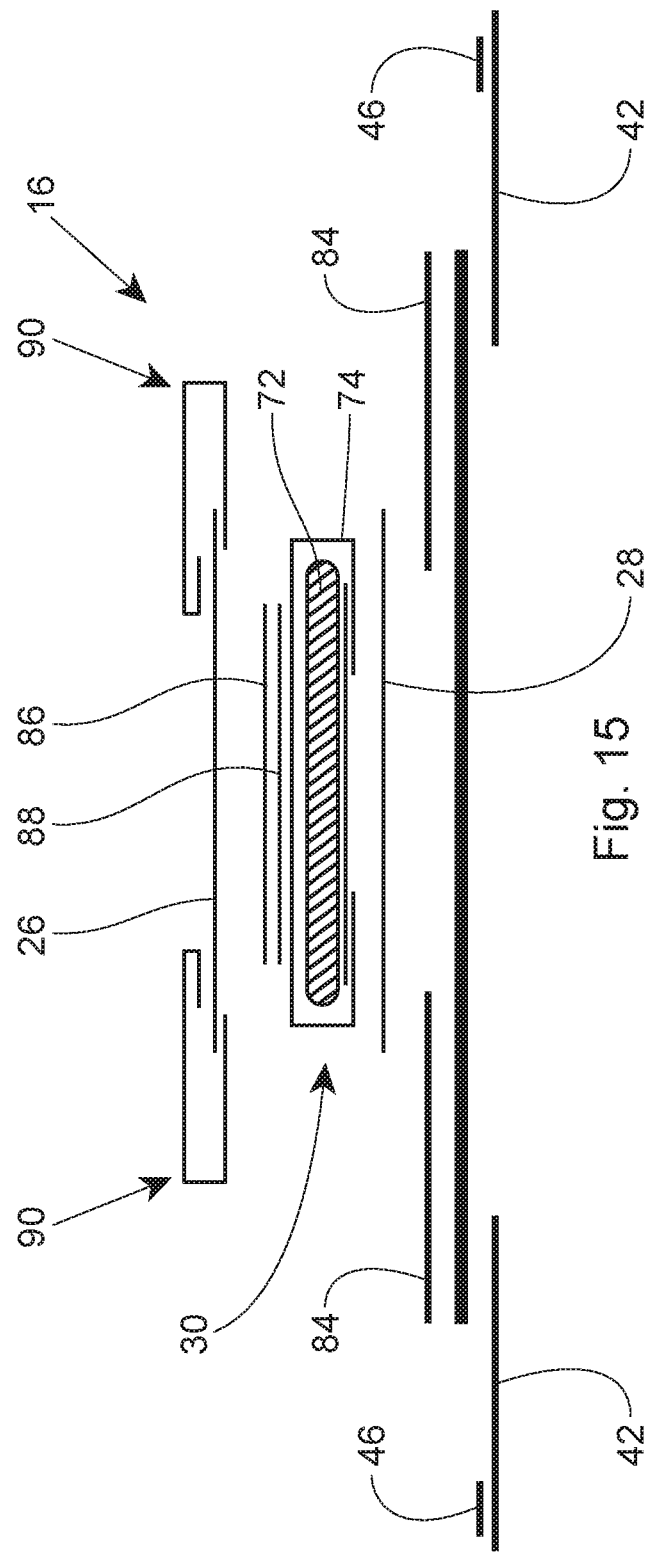
FIG. 15 is an example cross-sectional view taken within a back waist region of an absorbent article.

FIGS. 13-15 illustrate example cross-sectional views of absorbent articles within the scope of the present disclosure. FIG. 13 is an example cross-sectional view taken within a front waist region 12 of an absorbent article. FIG. 14 is an example cross-sectional view taken within a crotch region 14 of an absorbent article. FIG. 15 is an example cross-sectional view taken within a back waist region 16 of an absorbent article. In FIGS. 13-15, an outer cover material is element 40, a liquid permeable topsheet is element 26, opacity patches are elements 84, a liquid impermeable backsheet is element 28, an absorbent core is element 30, with the core bag being element 74, an absorbent material is element 72, and a distribution material is element 86. The distribution material 86 may comprise cross-linked cellulosic material and may be optional. An acquisition material is element 88. A liquid permeable topsheet is element 26. Barrier leg cuffs are elements 90. Elastics in the barrier leg cuffs are elements 92. Back ears are elements 42. Fasteners on the back ears 42 are elements 46. Construction glues and/or bonds between the various layers and/or components have been removed for clarity. Other cross-sectional configurations known to those of skill in the art are also within the scope of the present disclosure.

Figure 16:
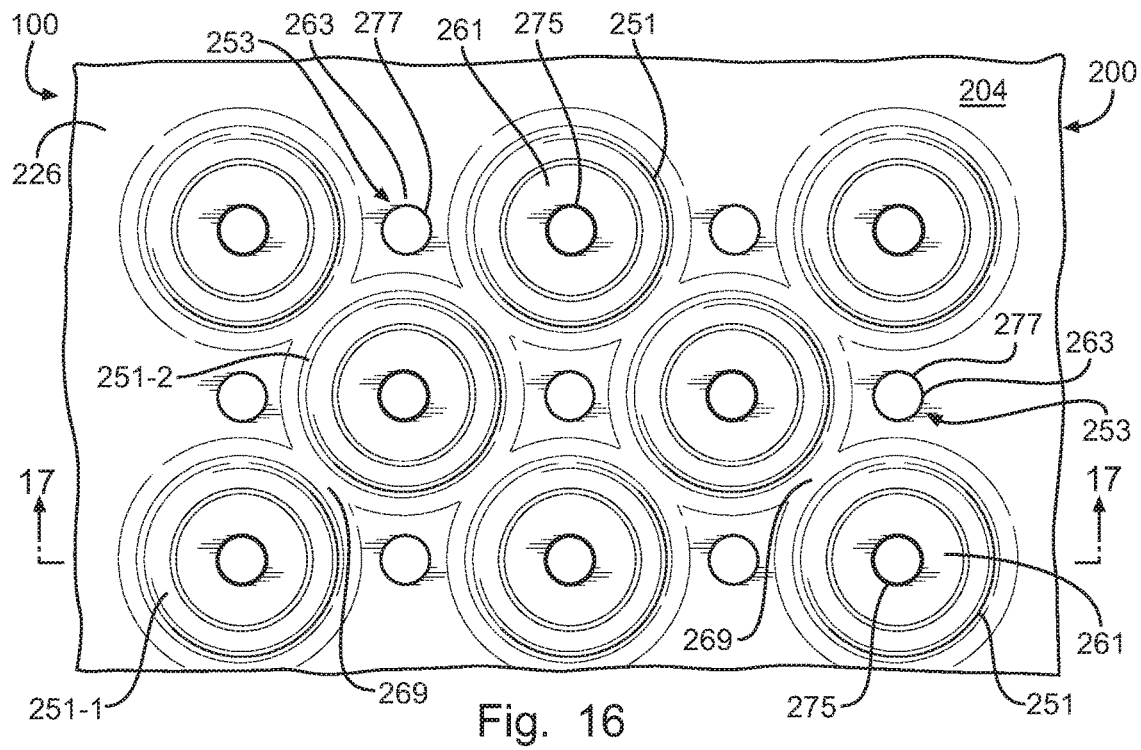
FIG. 16 is a detailed plan view of a portion of an example absorbent article, a wearer-facing surface facing the viewer, comprising a multi-layer material of the present disclosure, the material having a plurality of three-dimensional features in the form of raised areas and recesses, in which the raised areas and recesses comprise apertures.
Figure 17A:
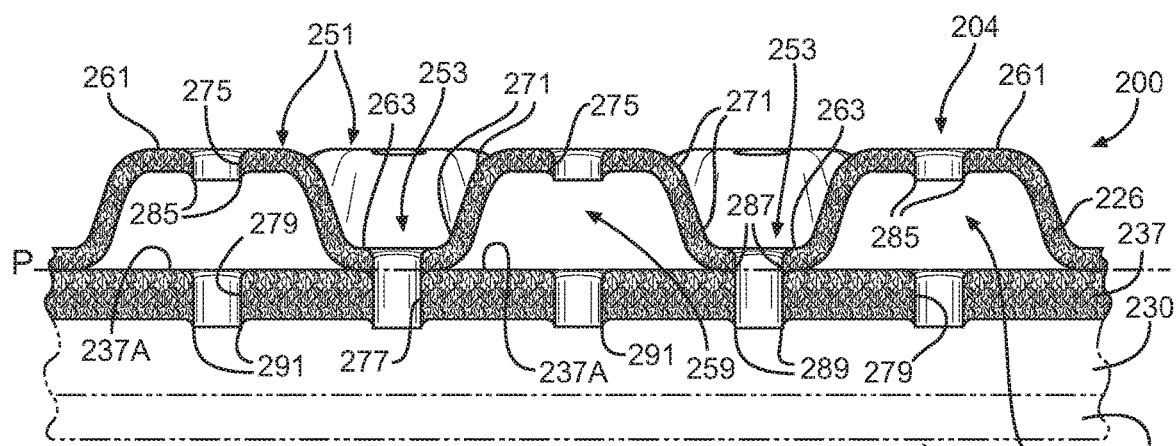
FIG. 17A is a cross-sectional view taken about line 17A-17A of FIG. 16.

General Structure and Properties of a Multi-Layer Material of an Absorbent Article FIG. 16 is a plan view of a portion of an example absorbent article 100 comprising a multi-layer material 200 according to the present disclosure, in which a wearer-facing surface 204 of the absorbent article 100 is facing the viewer. FIG. 17A is a cross-sectional view of the absorbent article 100 of FIG. 16 taken along view lines 17A-17A. FIGS. 18-21 are cross-sectional views, similar to FIG. 17A, of different aspects of an example absorbent article 100 comprising a multi-layer material 200, 200' according to the present disclosure. Unless otherwise noted, the structure and configuration of the example absorbent articles 100 illustrated in FIGS. 17A-C and 18-21 are substantially similar, and like reference numerals identify like elements.

With reference to FIGS. 16, 17A-17C and 18-21, the multi-layer material 200, 200' may comprise a liquid permeable topsheet 226 and a second material 237. The absorbent article 100 may comprise the multi-layer material 200, 200', a liquid impermeable backsheet 228, and an absorbent core 230 positioned at least partially intermediate the second material 237 and the backsheet 228, see FIG. 17A. The second material 237 may be positioned intermediate the topsheet 226 and the absorbent core 230 and may define one or more acquisition or distribution material layers or another layer of the topsheet 226. If the second material 237 discussed herein is another layer of the topsheet 226, one or more acquisition or distribution layers may also be provided in the example absorbent article 100. The topsheet 226 and the second material 237 together may be used as topsheets, outer cover nonwovens, acquisition layers, topsheet/acquisition layer laminates, topsheet/distribution layer laminates, or various other components of absorbent articles, for example. This description also applies to other example forms discussed herein. Further, a distribution layer may be positioned intermediate the second material 237 and the absorbent core 230. This distribution layer may comprise cross-linked cellulosic fibers, for example. Although a particular order of material layers is depicted herein, those of skill in the art will recognize that variances in this order may be possible.

The topsheet 226 and the second material 237, e.g., an acquisition material layer, may be formed from, or may comprise, nonwoven materials. The topsheet 226 and the second material 237 may comprise the same materials or different materials, or may comprise the same material with different treatments (e.g., one material may be more hydrophobic than the other material).

The nonwoven materials of the present disclosure may be made of any suitable nonwoven web materials ("precursor materials"). The nonwoven webs may be made from a single layer, or multiple layers (e.g., two or more layers, three or more layers, etc.). If multiple layers are used, they may be comprised of the same type of nonwoven material, or different types of nonwoven materials. In some cases, the precursor materials may be free of any film layers.

The fibers of the nonwoven precursor material(s) may be made of any suitable materials including, but not limited to natural materials, synthetic materials, and combinations thereof. Suitable natural materials may comprise, but are not limited to cellulose, cotton linters, bagasse, wool fibers, silk fibers, etc. Cellulose fibers may be provided in any suitable form, including but not limited to individual fibers, fluff pulp, drylap, liner board, etc. Suitable synthetic materials may comprise, but are not limited to nylon, rayon and polymeric materials. Suitable polymeric materials may comprise, but are not limited to: polyethylene (PE), polyester, polyethylene terephthalate (PET), polypropylene (PP), and co-polyester. In some forms, however, the nonwoven precursor materials may be either substantially, or completely free, of one or more of these materials. For example, in some forms, the precursor materials may be substantially free of cellulose, and/or exclude paper materials. In some forms, one or more precursor materials may comprise up to 100% thermoplastic fibers. The fibers in some cases may, therefore, be substantially non-absorbent. In some forms, the nonwoven precursor materials may be either substantially, or completely free, of tow fibers.

The nonwoven precursor webs may be formed from various suitable processes, such as, for example, air laying processes, wetlaid processes, meltblowing processes, spunbonding processes, and carding processes. The fibers in the webs may then be bonded via spunlacing processes, hydroentangling, calendar bonding, through-air bonding and resin bonding. Some of such individual nonwoven webs may have bond sites where the fibers are bonded together.

The basis weight of nonwoven materials is usually expressed in grams per square meter (gsm). The basis weight of a single layer nonwoven material may range from about 8 gsm to about 100 gsm, depending on the ultimate use of the material. For example, the topsheet 226 may have a basis weight from about 8 to about 40 gsm, from about 8 to about 30 gsm, or from about 8 to about 20 gsm, for example. An acquisition layer (second material 237) may have a basis weight from about 10 to about 120 gsm, from about 10 to about 100 gsm, or from about 10 to about 80 gsm, for example. Hence, the basis weight of the second material 237 (e.g., a single acquisition layer) may be greater than the basis weight of the topsheet 226. The basis weight of a multi-layer material is the combined basis weight of the constituent layers and any other added components. The basis weight of multi-layer materials of interest herein (e.g., a topsheet 226 and a single acquisition layer defining the second material 237) may range from about 20 gsm to about 150 gsm, depending on the ultimate use of the material. The nonwoven precursor webs may have any suitable density.

The precursor nonwoven webs may have certain desired characteristics. It is typically desirable for the precursor nonwoven web materials to have extensibility to enable the fibers to stretch and/or rearrange into the form of the protrusions (raised areas) and/or recesses. If the nonwoven webs are comprised of two or more layers, it may be desirable for all of the layers to be as extensible as possible. It may also be desirable for the precursor nonwoven webs to be capable of undergoing plastic deformation to ensure that the structure of the deformations is "set" in place so that the nonwoven web will not tend to recover or return to its prior configuration. The nonwoven webs may include multicomponent fibers with a suitable denier (i.e., linear mass density) to achieve these desired characteristics and to balance the potentially conflicting requirements of (i) softness, (ii) barrier capability, (iii) formation, strength, and extensibility during stretching (e.g., by ring rolling), and (iv) the economics of fiber spinning. For example, the multicomponent fibers may have a linear mass density of between 1 and 5 denier per filament.

When the nonwoven web comprises two or more layers, the different layers may have the same properties, or any suitable differences in properties relative to each other. One of the layers, may serve as the topsheet 226, and one or more other layers may define the second material 237 and comprise one or more acquisition layers. The acquisition layer(s) receives liquids that pass through the topsheet 226 and acquires and/or distributes them, for example, to the underlying absorbent core 230. In some forms, the topsheet 226 may comprise a hydrophobic material, and the second material 237 may comprise a hydrophilic material. In some forms, the topsheet 226 may be more hydrophobic than the second material 237. In other particular forms, the topsheet 226 may be less hydrophilic than the second material 237, which may lead to better dewatering of the topsheet 226. Hence, a hydrophilicity gradient may be defined such that it extends from a wearer-facing surface of the topsheet 226 to a garment-facing surface of the second material 237 and increases from the wearer-facing surface of the topsheet 226 to the garment-facing surface of the second material 237. In other forms, the topsheet 226 may be more hydrophilic than the second material 237.

In other forms, the different layers of the multi-layer material 200 may have different opacities as compared to each other. In some examples, an opacity of each layer of material may be greater than 40%; the opacity of a second layer of material, e.g., the second material 237, may be at least 5% higher than an opacity of a first layer of material, e.g., the topsheet 226; and the total or combined opacity of the absorbent article 100 may be greater than 60%. In some particular examples, the opacity of the topsheet 226 may be about 48%, the opacity of the second material 237 may be about 56%, and the total opacity of the absorbent article 100 may be about 70%. In further forms, one or more of the layers of the multi-layer material 200 may comprise different colors.

Two or more layered nonwoven webs may be combined together in any suitable manner. In some cases, the layers may be unbonded to each other and held together autogenously (that is, by virtue of the formation of deformations therein). In other aspects, the layers may be joined together by other mechanisms. If desired, an adhesive between the layers, ultrasonic bonding, chemical bonding, resin or powder bonding, thermal bonding, or bonding at discrete sites using a combination of heat and pressure may be selectively utilized to bond certain regions or all of the precursor webs. In addition, the multiple layers may be bonded during processing, for example, by carding one layer of nonwoven onto a spunbond nonwoven and thermal point bonding the combined layers. In some cases, certain types of bonding between layers may be excluded. For example, the layers of the present structure may be non-hydroentangled together. In some particular embodiments according to the present disclosure, the topsheet 226 may be joined to the second material 237 using one of heat embossing or an adhesive.

With reference to FIGS. 16 and 17A, the topsheet 226 may comprise a plurality of three-dimensional elements in the form of raised areas 251 and recesses 253. The second material 237 may comprise a generally planar material defining a plane P along its wearer-facing surface. The term "generally planar" is not meant to imply any particular flatness, smoothness, or dimensionality. Thus, the substantially planar material of the second material 237 may include other features that provide the second material 237 with a topography. Such other features may include, but are not limited to small projections, raised network regions, and other types of features. Thus, the substantially planar material of the second material 237 is generally planar when considered relative to the raised areas 251 and recesses 253.

In some aspects, the topsheet 226 and the second material 237 may each comprise a single layer of material, as shown in FIGS. 17A and 18-20. In other aspects, one or both of the topsheet 226 and the second material 237 may comprise two or more layers of material. In aspects in which the topsheet 226 comprises two or more layers of material, one layer may comprise a cotton-containing layer and another layer may comprise a non-cotton containing layer, see FIGS. 23 and 24 and the corresponding discussion below. In aspects in which the second material 237 comprises two or more layers of material, one layer may comprise a cotton-containing layer and another layer may comprise a non-cotton containing layer, see FIGS. 21, 26, and 27 and the corresponding discussion below. In all aspects, the cotton-containing layer may comprise about 1% cotton to about 25% cotton, about 5% cotton to about 20% cotton, or about 5% cotton to about 15% cotton, and the cotton may be hydrophobic. In all aspects, the second material 237 may have a higher linear mass density, i.e., denier per filament, than a denier per filament of the topsheet 226.

Each raised area 251 in FIGS. 16 and 17A comprises sidewalls 271 and an upper portion defined by a substantially planar outer portion 261, in which the sidewalls 271 extend substantially outwardly in a direction away from the second material 237 and the plane P to the planar outer portion 261. The sidewalls 271 may be substantially linear, as shown in the aspects depicted in FIGS. 16 and 17A. In other aspects, the sidewalls 271 may be curved along at least a section of the raised areas 251. The planar outer portion 261 on each raised area 251 may comprise a substantially central location comprising an upper center point or an upper center section including the upper center point. Substantially any point on the raised area planar outer portion 261 may define a crest or apex, which may comprise a highest point of the raised area 251.

The recesses 253 are adjacent to and located between the raised areas 251 and share topsheet sidewalls 271 with adjacent raised areas 251. Hence, each recess 253 comprises sidewalls 271 extending in a direction toward the plane P, as well as a trough or a base defined by a substantially planar portion 263. The substantially planar portion or base 263 of each recess 353 comprises a substantially central location comprising a lower center point or a lower center section including the lower center point. Substantially any point on the recess planar portion or base 263 may comprise a lowest point of the recess 253. Thus, the substantially central locations of the planar outer portions 261 of the raised areas 251 may each comprise the point or section that is positioned most distal from the central locations of the substantially planar portions or bases 263 of the recesses 253 and from the plane P, and the central locations of the substantially planar portions or bases 263 of the recesses 253 may each comprise the point or section that is positioned most distal from the substantially central locations of the substantially planar outer portions 261 of the raised areas 251.

In other aspects, the upper portions of the raised areas 251 and/or the bases of the recesses 253 may comprise a substantially convex or dome-shaped portion (i.e., shaped similar to a partial sphere), and in further aspects, may have a parabolic shape in cross section, a substantially conical or frustoconical shape, or any other curvilinear cross-section or configuration. In yet further aspects, a substantially planar web of topsheet material may be deformed at predefined locations in a direction away from an initial plane of the web of topsheet material to create the raised areas 251 and recesses 253 such that the raised areas 251 may be deformed into the web of topsheet material to extend above the initial plane of the web of topsheet material and the recesses 253 may be deformed into the web of topsheet material to extend below the initial plane of the web of topsheet material.

The topsheet 226 may also comprise substantially planar sections 269 located between pairs of adjacent raised areas 251, i.e., between diagonally positioned raised areas 251-1 and 251-3 as shown in FIG. 16. The substantially planar sections 269 may generally be positioned in a plane parallel to or in the same plane as plane P.

The three-dimensional features, i.e., the raised areas 251 and recesses 253, may be disposed in any suitable density across the surface of the multi-layer material 200, 200'. The features may, for example, be present in a density of: from about 20 to about 200 features; from about 30 to about 150 features, from about 40 to about 130 features; from about 60 to about 100 features, in an area of 10 cm².

A void 259 may be defined between each raised area 251 and a corresponding substantially planar area 237A of a wearer-facing surface of an adjacent layer of material. In the FIG. 17A aspect, the planar areas 237A may form part of a wearer-facing surface of a substantially planar region of the second material 237. For example, the voids 259 may be defined in the raised areas 251 intermediate a garment-facing surface of the topsheet 226 and the wearer-facing surface of the substantially planar region of the second material 237, as shown in the aspect illustrated in FIGS. 17A and 18-21. The topsheet 226 may be free from contact with the second material 237 in the raised areas 251. The topsheet 226 may be joined to the second material 237 in the recesses 253, e.g., at one or more points along the substantially planar portions 263 of the recesses 253. In some aspects, the topsheet 226 may also be joined to the second material 237 at the generally planar sections 269 (see FIG. 16). The voids 259 provide void volume for BM or other bodily fluid retention so that BM or other bodily fluids may pass to the second material 237 and be absorbed into the second material 237 and the absorbent core 230 or may be at least partially dewatered by the second material 237 and the absorbent core 230.

A width or circumference of each raised area 251 may be greatest at a point nearest the plane P. For example, in the aspect shown in FIG. 17A, the linear sidewalls 271 defining each raised area 251 may slope substantially continuously, along at least a section of the raised area 251, toward the substantially planar outer portion 261 of the raised area 251. In other aspects, the sidewalls 271 may extend outwardly substantially perpendicular to the plane P, and the width or circumference of the raised areas 251 may remain substantially the same along at least a portion of the raised area 251 from the point nearest the plane P toward the substantially planar outer portion 261. In further aspects in which one or more sections of the sidewalls 271 may be curved, the sidewalls 271 may curve substantially continuously, along at least a section of the raised area 251, toward the substantially planar outer portion 261.

One or more apertures may be formed in the topsheet 226, the second material 237, and/or one or more other components of the absorbent article 100. The apertures may extend completely or partially through a thickness of the respective component(s). In the aspects illustrated in FIGS. 16-18, a first aperture 275 may be formed in the substantially central location of the substantially planar outer portion 261, e.g., at the upper center point, of each of at least a majority of the raised areas 251. The apertures 275 may extend completely through a thickness of the topsheet 226. The apertures 275 formed in the raised areas 251 may be in fluid communication with the voids 259. In some aspects, the raised areas 251 may each comprise two or more apertures.

Figure 18:
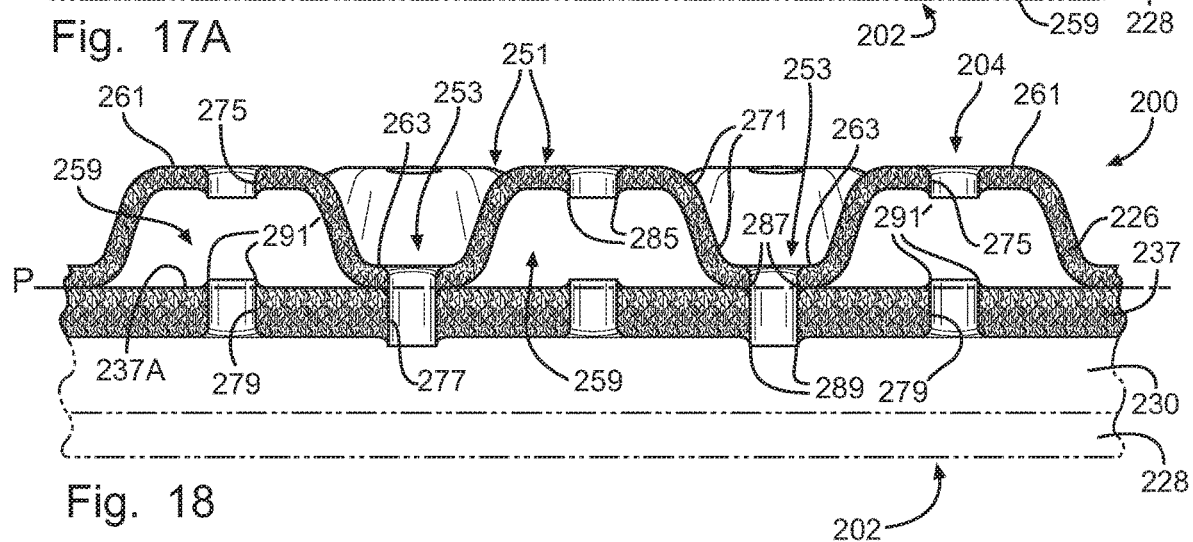
FIGS. 18-21 are cross-sectional views, similar to FIG. 17A, of alternative aspects of an example absorbent article comprising a multi-layer material having a plurality of three-dimensional features in the form of raised areas and recesses, in which the raised areas and recesses comprise apertures.
Figure 19:
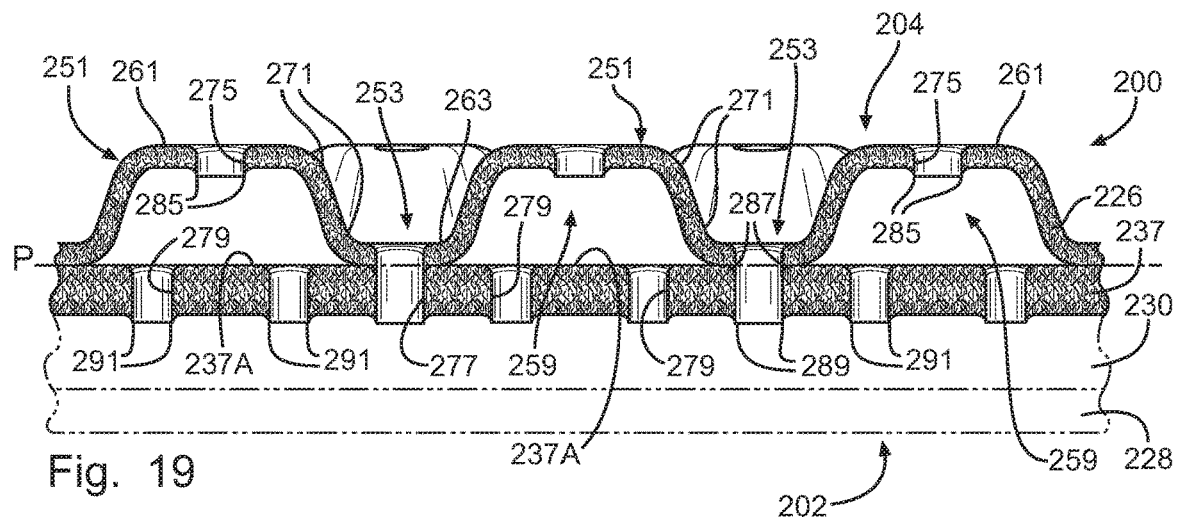
Figure 20:
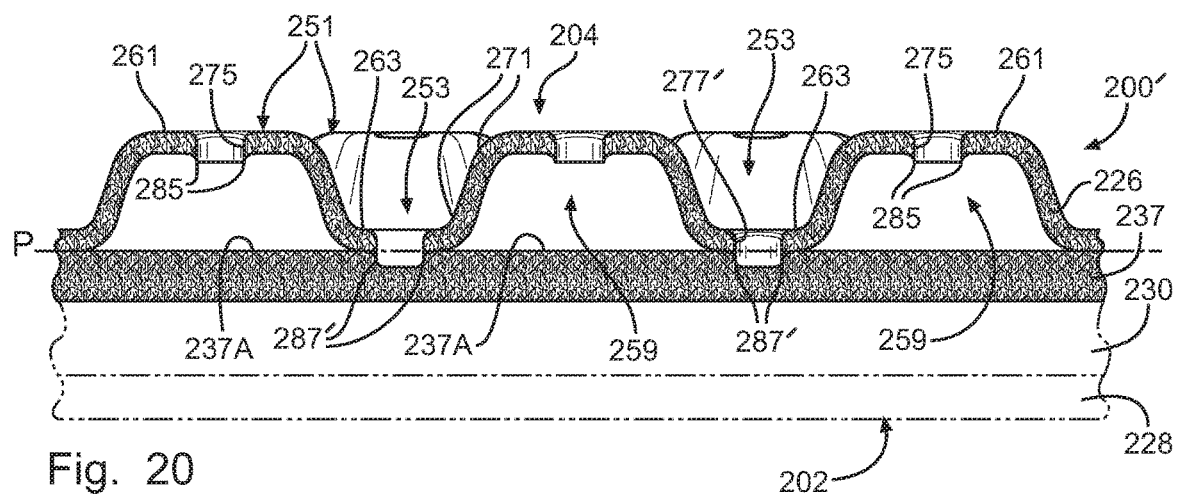
Figure 21:
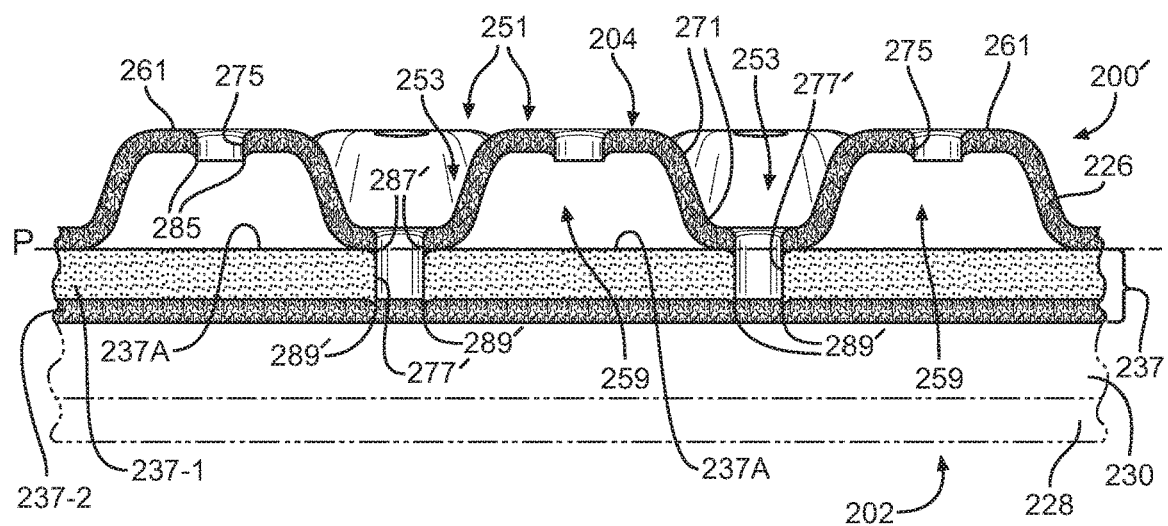

A second aperture 277 may be formed in the central location of the planar portion or base 263, e.g., at the lower center point of the base central location, of each of at least a majority of the recesses 253. In some aspects, the recesses 253 may each comprise two or more apertures. As seen in FIGS. 17A, 18, and 19, the aperture 277 may extend completely through a thickness of both the topsheet 226 and the second material 237. In the aspects depicted in FIGS. 20 and 21, the apertures 277' formed in at least a portion of the recesses 253 extend completely through the topsheet 226 but extend only partially through the second material 237 (within normal manufacturing tolerances). Having apertures 277' that extend only through the topsheet 226 and only partially through the second material 237 may at least inhibit materials underneath the second material 237 from approaching a wearer's skin through the apertures 277'. In FIG. 20, the second material 237 comprises a single layer of material, e.g., a nonwoven material as described herein, and the apertures 277' extend completely through the topsheet 226 and only partially through the single-layer second material 237. In FIG. 21, the second material 237 comprises two or more layers of nonwoven material, e.g., a first layer 237-1 and a second layer 237-2, in which the apertures 277' extend completely through the topsheet 226 and the first layer 237-1 of the second material 237 but do not extend through the second layer 237-2 of the second material 237.

As described above, one or both of the first layer 237-1 and the second layer 237-2 of the second material 237 may comprise a cotton-containing material, see for example FIG. 21. In some particular aspects, the first layer 237-1 of the second material 237, e.g., the layer on the wearer-facing surface of the second material 237, may comprise the cotton-containing material, in which the cotton-containing material may be hydrophobic. Aspects in which the first layer 237-1 of the second material 237 comprises the cotton-containing material may have the additional benefit that the cotton-containing first layer 237-1 of the second material 237 may be sandwiched between the topsheet 226 and the second layer 237-2 of the second material 237, which reduces the amount of cotton fiber and dust buildup on the machinery during the aperturing process and also minimizes the amount of cotton fibers that is exposed to and reaches the skin of the wearer. In other particular aspects, the second layer 237-2 of the second material 237, e.g., the layer on the garment-facing surface of the second material 237, may comprise the cotton-containing material, in which the cotton-containing material may be hydrophobic.

As shown in FIGS. 17A, 18, and 19, one or more third apertures 279 may be formed in the substantially planar areas 237A of the second material 237 under at least a majority of the raised areas 251. Each third aperture 279 may extend completely or partially through a thickness of the second material 237. In the aspects shown in FIGS. 17A and 18, a third aperture 279 may be formed in a substantially central location of the substantially planar area 237A of the second material 237 enclosed by the respective raised area 251. The third aperture 279 formed in the central location of the second material 237 may be substantially in alignment with the first aperture 275 formed in the central location of the raised area 251 when viewed looking at the wearer-facing surface as in FIG. 16, see also FIGS. 17A and 18. In other aspects, the one or more first apertures 275 formed in the substantially planar outer portions 261 of the raised areas 251 and the one or more third apertures 279 formed in the second material 237 may be spaced apart from each other in a direction generally parallel to the plane P such that the first and third apertures 275, 279 are not in alignment. For example, as illustrated by the FIG. 19 aspect, the second material 237 may comprise two third apertures 279 that are not in alignment with the one first aperture 275 formed in the raised area 251. One or three or more third apertures 279 may also be provided in the second material 237 under a corresponding raised area 251. In further aspects, such as those depicted in FIGS. 20 and 21, no apertures are formed in the second material 237 under the raised areas 251 such that these portions of the second material 237 under the raised areas 251 comprise a substantially continuous sheet.

Some current two-dimensional apertured topsheets are effective at allowing BM to pass through the topsheet into the layers below. These two-dimensional apertured topsheets, however, provide very little void volume under the topsheets in that the generally planar topsheets are in a facing relationship with the generally planar layer below (typically an acquisition layer). Thus, the BM or other bodily fluid acquisition of these two-dimensional apertured topsheets has limitations. The three-dimensional nonwoven materials of the present disclosure having apertures provide an improvement in BM or other bodily fluid acquisition, while also providing reduced skin marking and improved softness.

By providing one or more apertures in a majority of the raised areas 251 and recesses 253 and in the second material 237 under the raised areas 251, BM and bodily fluids may be better absorbed and, in the context of an absorbent article, wicked toward the absorbent core 230. In particular, enhanced flow occurs of viscous fluids, such as runny BM, towards the absorbent core 230 and away from the wearer-facing surface of the topsheet 226 and the skin of a wearer. The first apertures 275 on the raised areas 251 allow the viscous fluids to more easily access the volume of the voids 259 below the raised areas 251, and the third apertures 279 formed in the second material 237 under the raised areas 251 allow the fluids to more quickly and easily reach the absorbent core 230. The second apertures 277, 277' in the recesses 253 reduce the likelihood that viscous fluids may pond in the recesses 253 instead of being absorbed by the second material 237 and the absorbent core 230.

BM or other bodily fluids are able to bypass some of the resistance to acquisition of the topsheet 226 and the acquisition layer(s) (e.g., the second material 237), thereby reducing BM, or other bodily fluid, spreading (i.e., run-off) (especially when the BM, or other bodily fluids are within the voids 259). The first and second apertures 275, 277, 277' in the raised areas 251 and recesses 253 also allow the topsheet 226 to acquire urine better while being less hydrophilic or hydrophobic than typical topsheets, thereby leading to better dryness, especially with relatively large aperture dimensions (e.g., greater than 0.75 mm in width and/or length, greater than 1.0 mm in width and/or length, greater than 1.5 mm in width and/or length, or greater than 2.0 mm in width and/or length, for example).

As noted above, in some aspects, a hydrophilicity gradient may be defined such that it extends from the wearer-facing surface of the topsheet 226 to the garment-facing surface of the second material 237 and increases from the wearer-facing surface of the topsheet 226 to the garment-facing surface of the second material 237. In these aspects, quick absorption of urine occurs through the apertures 275, 277, 277' in the raised areas 251 and the recesses 253, while leaving a relatively dry topsheet 226, being drained from urine due to the hydrophilicity gradient. This dryer, wearer-facing surface 204 may also lead to reduced skin marking or red marking.

The first, second and third apertures 275, 277, 277', 279 may comprise any suitable shape, including cylindrical, ovate, diamond-shaped, etc., when viewed from the wearer-facing surface of the topsheet 226. In some aspects, a major axis, e.g., a longitudinal axis LA, defining a length of each aperture may be less than 4 mm, see second aperture 277 in FIG. 17B. The first and third apertures 275 and 279 may have substantially the same shape and size as the second aperture 277. In some particular aspects, the longitudinal axis LA of each aperture may be less than 3 mm. Depending on the shape of the aperture, an axis TA defining a width of each aperture and being substantially transverse to the longitudinal axis LA may be less than or equal to the longitudinal axis LA. In some aspects, the apertures may all be of a similar size and/or shape, and in other aspects, the apertures may be of a different size and/or shape. For example, the third apertures 279 formed in the substantially planar areas 237A of the second material 237 under the raised areas 251 may comprise multiple smaller apertures, see FIG. 19, in place of, or in addition to, the apertures 279 depicted in FIGS. 17A and 18. For apertures having a cylindrical shape, the longitudinal and transverse axes LA and TA may be generally equal and define a cylinder diameter. In the depicted aspects, a thickness T of the second apertures 277 parallel to a vertical axis VA, wherein the vertical axis VA is perpendicular to the longitudinal and transverse axes LA and TA, may be substantially uniform through the entire thickness of the topsheet 226 ($T_{TS}$) and/or second material 237 ($T_{SM}$) when viewed in cross-section, see FIG. 17C. The topsheet 226 may have a thickness $T_{TS}$ of from about 0.2 mm to about 1.5 mm and the second material 237 may have a thickness $T_{SM}$ from about 0.2 mm to about 4.0 mm, see FIG. 17C.

Any suitable processes for forming the first, second and third apertures 275, 277, 277', 279 may be utilized. For example, the apertures in the materials of the present disclosure may be formed by hydroforming carded webs, laser cutting, punching with a patterned roll, using hot pin methods, overbonding and ring rolling aperturing, as disclosed in U.S. Patent Application Publication No. US 2016/0136014 and U.S. Pat. No. 5,628,097, the disclosures of which are incorporated herein by reference, or other suitable methods. Alternatively, additional aperturing processes may be used such as described in U.S. Pat. Nos. 9,023,261, 8,158,043, 8,241,543, and 8,679,391, the disclosures of which are incorporated herein by reference.

The sections of the raised areas 251 and the recesses 253 intermediate the apertures 275, 277, 277' may be continuous and contain no additional apertures. For example, as seen in FIGS. 17A and 18-21, the sidewalls 271 defining the raised areas 251 and the recesses 253 and extending between the apertures 275, 277 are continuous and are free of any additional apertures. It is believed that by forming the raised areas 251 and the recesses 253 without apertures in the sidewalls 271, the strength of the raised areas 251 and recesses 253 may be enhanced so as to reduce the likelihood that the raised areas 251 and/or recesses 253 may collapse under in-bag compression or compression caused by a wearer.

Figure 17B:
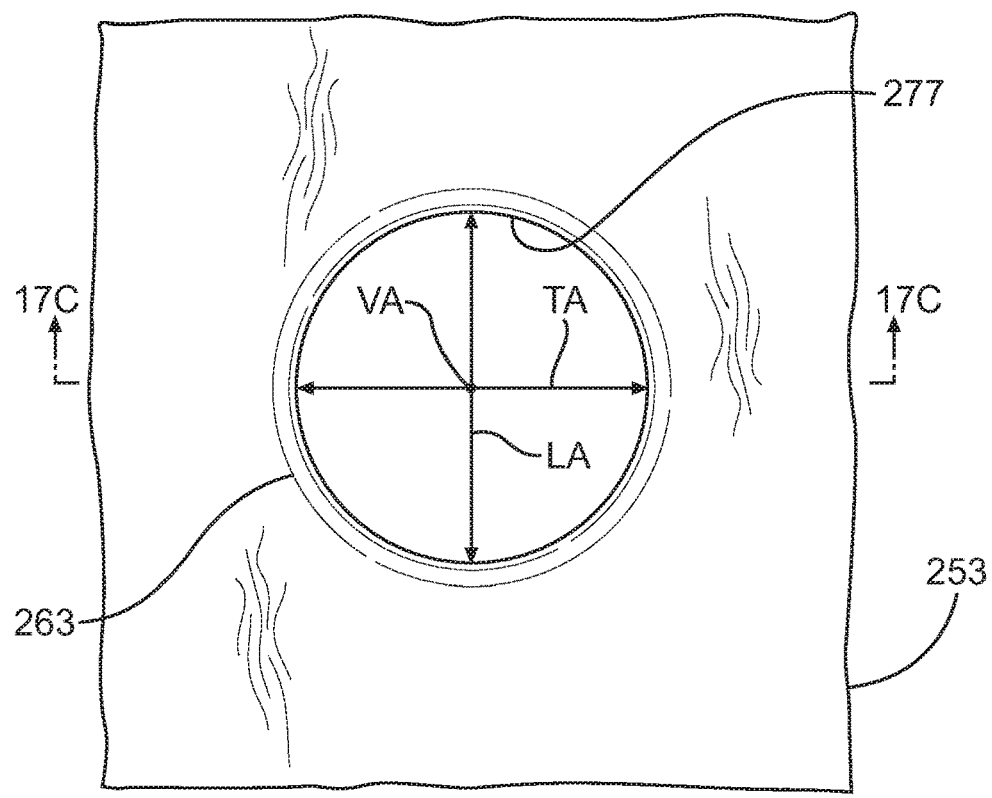
FIG. 17B is an enlarged view of a raised area or a recess aperture of FIG. 16.
Figure 17C:
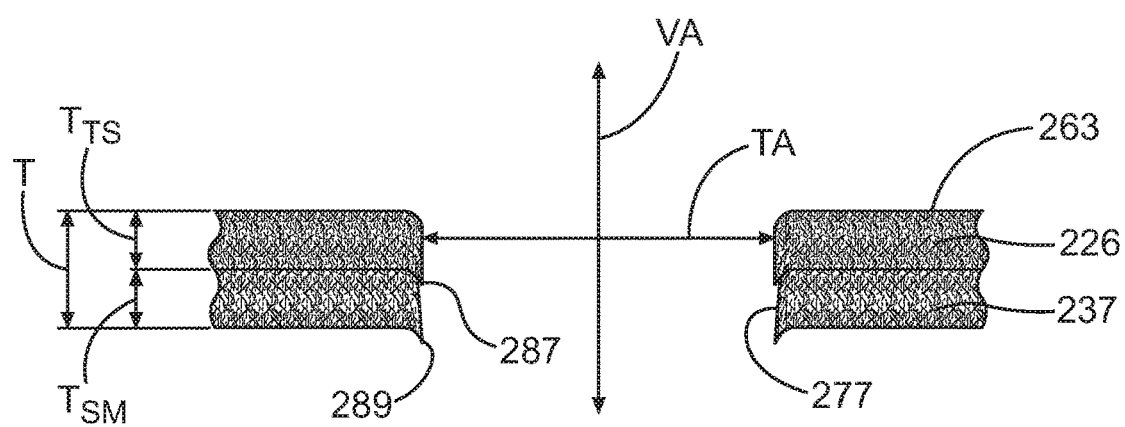
FIG. 17C is a cross-sectional view taken along section line 17C-17C in FIG. 17B.

With reference to FIGS. 17A and 18-21, the raised area planar outer portions 261, the recess planar portions or bases 263, and the second material planar areas 237A in which the apertures 275, 277, 277', 279 are formed may comprise small pieces or flaps of material that remain attached to circumferential edges of the apertures 275, 277, 277', 279 following manufacture of the absorbent article 100. In some aspects, the flaps may extend at least partially into, and be joined to, an adjacent layer of material, and in other aspects, the flaps may extend into an open space, e.g., the voids 259. As shown in FIG. 17A, the first apertures 275 formed in the planar outer portions 261 of the raised areas 251 may have flaps 285 comprising portions of the topsheet 226. The second apertures 277 formed in the recesses 253 may have similar flaps 287 comprising portions of the topsheet 226, and in some aspects, the apertures 277 may further comprise flaps 289 comprising portions of the second material 237. The third apertures 279 formed in the second material 237 under the raised areas 251 may also have similar flaps 291 comprising portions of the second material 237. As best seen in FIG. 17C, which is a detailed view of one of the second apertures 277 formed in the substantially planar portion 263 of one of the recesses 253 of any of FIG. 17A, 18, or 19, the flaps 287, 289 may give the aperture 277 a substantially conical or frustoconical shape, e.g., a shape that narrows at one end toward a garment-facing surface 202 of the absorbent article 100 along at least a portion of the vertical axis VA of the aperture 277. In other aspects, the apertures 275, 277, 277', 279 do not form conical shapes.

In the aspects shown in FIGS. 17A and 18-21, the flaps 285 formed in the substantially planar outer portions 261 of the raised areas 251 may extend into the voids 259 toward the plane P and toward the garment-facing surface 202 of the absorbent article 100. In some aspects, the flaps 285 may extend toward the wearer-facing surface 204 of the absorbent article 100. In some further aspects where the topsheet 226 comprises two or more layers, the flaps 285 may extend at least partially into an adjacent layer of material.

The flaps 287, 289 formed in the recesses 253 may extend toward the garment facing surface 202 at least partially into an adjacent layer of material. For example, as shown in FIGS. 17A, 18, and 19, the flaps 287 formed from the topsheet 226 may extend at least partially into the second material 237, and the flaps 289 formed from the second material 237 may extend at least partially into a material layer below the second material 237, e.g., the absorbent core 230. In the aspects depicted in FIGS. 17A and 19, the flaps 291 formed in the second material 237 under the raised areas 251 may extend at least partially into a material layer below second material 237, e.g., the absorbent core 230. In the FIG. 18 aspect, the flaps 291' formed in the second material 237 under the raised areas extend into the voids 259 toward the wearer-facing surface 204 of the absorbent article 100.

In the FIG. 20 aspect in which the apertures 277' extend only partially through the second material 237, flaps 287' comprising portions of the topsheet 226 may extend partially into the second material 237. Where the second material 237 comprises two or more layers, e.g., first and second layers 237-1 and 237-2, see FIG. 21, the flaps 287' comprising portions of the topsheet 226 may extend at least partially into the first layer 237-1 of the second material 237, and flaps 289' comprising portions of the first layer 237-1 of the second material 237 may extend partially into the second layer 237-2 of the second material 237.

The flaps extending into an adjacent layer of material may help to stabilize the contact point(s) between the layers of the absorbent article 100 and may help prevent tearing of, for example, the topsheet 226. In addition, the extension of the flaps into, and joinder to, an adjacent layer of material may help prevent the flaps from moving toward the plane P and fully or partially closing the associated aperture, which may result in reduced fluid absorption and retention. The second material flaps 291' extending into the voids 259, see FIG. 18, may help with absorption of fluid into the absorbent article 100, particularly when the topsheet 226 is less hydrophilic than the second material 237.

As shown in the FIG. 17A aspect, the flaps 285, 287, 289, 291 may all extend in a same direction, e.g., toward the garment-facing surface 202 of the absorbent article 100. In other aspects, one or more of the sets of flaps may extend in a different direction. For example, as shown in FIG. 18, the apertures 279 formed in the second material 237 under the raised areas 251 comprise flaps 291' that extend in an opposite direction, e.g., toward the wearer-facing surface 204, as compared to the flaps 285, 287, 289 located in the raised areas 251 and recesses 253.

Figure 22:
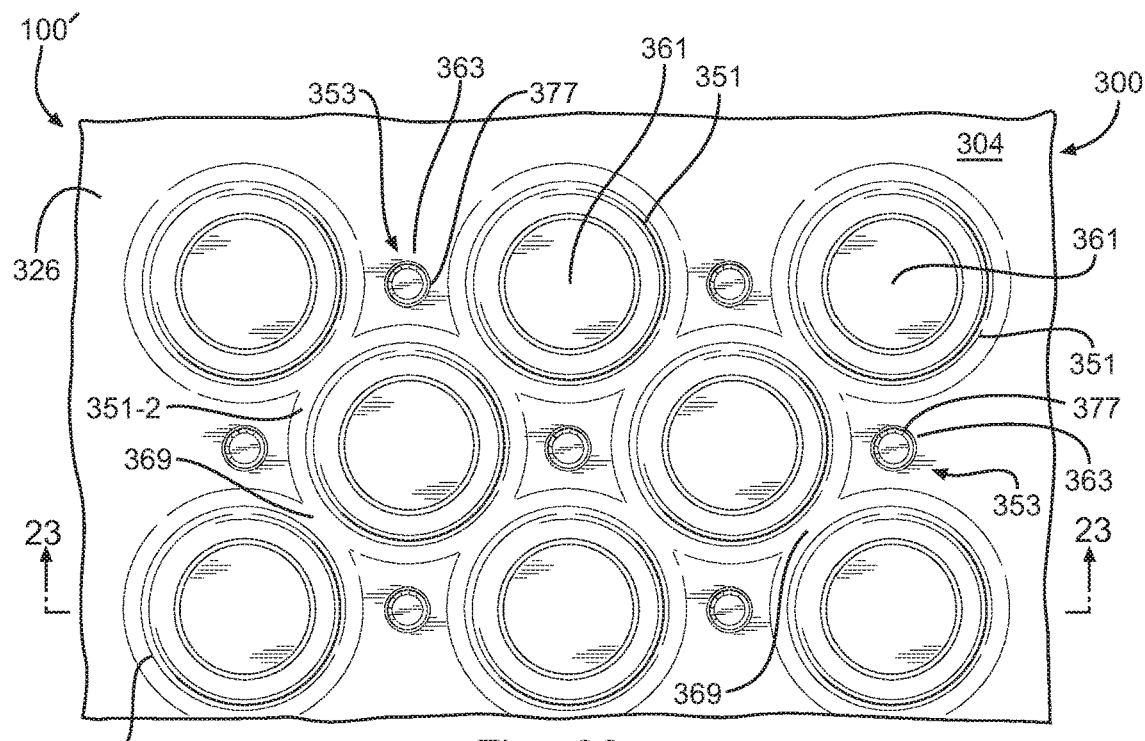
FIG. 22 is a detailed plan view of a portion of another example absorbent article, a wearer-facing surface facing the viewer, comprising a multi-layer material of the present disclosure, the material having a plurality of three-dimensional features in the form of raised areas and recesses, in which the recesses comprise apertures.
Figure 23:
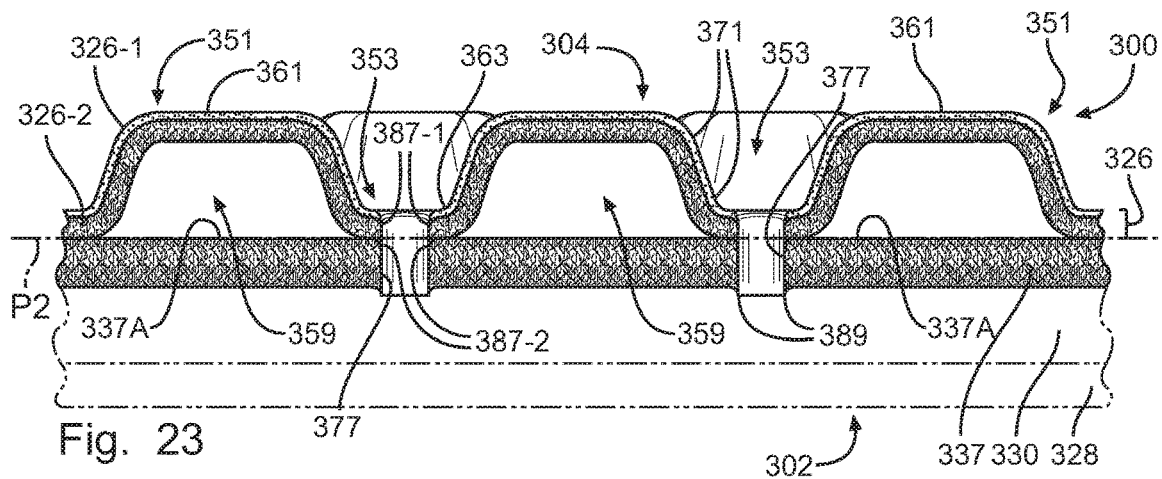
FIG. 23 is a cross-sectional view taken about line 23-23 of FIG. 22.

FIG. 22 is a plan view of a portion of another example absorbent article 100' comprising a multi-layer material 300 according to the present disclosure, in which a wearer-facing surface 304 of the absorbent article 100' is facing the viewer. FIG. 23 is a cross-sectional view of the absorbent article 100' of FIG. 22 taken along view lines 23-23. FIGS. 24-27 are cross-sectional views, similar to FIG. 23, of different aspects of an example absorbent article 100' comprising a multi-layer material 300, 300' according to the present disclosure. Unless otherwise noted, the structure and configuration of the example absorbent articles 100' illustrated in FIGS. 23-27 are substantially similar, and like reference numerals identify like elements. Although a particular order of material layers is depicted herein, those of skill in the art will recognize that variances in this order may be possible.

With reference to FIGS. 22-27, the multi-layer material 300, 300' may comprise a liquid permeable topsheet 326 and a second material 337. The absorbent article 100' may comprise the multi-layer material 300, 300', a liquid impermeable backsheet 328, and an absorbent core 330 positioned at least partially intermediate the second material 337 and the backsheet 328, see FIG. 23. The second material 337 may be positioned intermediate the topsheet 326 and the absorbent core 330 and may define one or more acquisition or distribution material layers or another layer of the topsheet 326. If the second material 337 discussed herein is another layer of the topsheet 326, one or more acquisition or distribution layers may also be provided in the example absorbent article 100'.

The topsheet 326 and second material 337 may be formed from the same nonwoven web materials used to form the topsheet 226 and second material 237 of the aspect of FIGS. 16 and 17A-17C described above. In particular, the topsheet 326 and the second material 337 may each comprise a single layer of material in some aspects, see FIG. 25, and in other aspects, one or both of the topsheet 326 and the second material 337 may comprise two or more layers of material, see FIGS. 23, 24, 26, 27. In aspects in which the topsheet 326 and/or the second material 337 comprise two or more layers of material, one layer may comprise a cotton-containing layer and another layer may comprise a non-cotton containing layer. In all aspects, the cotton-containing layer may comprise about 1% cotton to about 25% cotton, about 5% cotton to about 20% cotton, or about 5% cotton to about 15% cotton, and the cotton may be hydrophobic. In all aspects, the second material 337 may have a higher denier per filament than a denier per filament of the topsheet 326.

With reference to FIGS. 22 and 23, the topsheet 326 may comprise a plurality of three-dimensional features in the form of raised areas 351 and recesses 353. The second material 337 may comprise a generally planar material defining a plane P2 along its wearer-facing surface. Each raised area 351 comprises sidewalls 371 and an upper portion defined by a substantially planar outer portion 361, in which the sidewalls 371 extend upward in a direction away from the second material 337 and the plane P2 to the planar outer portion 361. The sidewalls 371 may be substantially linear as shown in FIG. 23. In other aspects, the sidewalls 371 may be curved along at least a section of the raised areas 351. The recesses 353 are adjacent to and located between the raised areas 351 and share topsheet sidewalls 371 with adjacent raised areas 351. The recesses 353 extend in a direction toward the second material 337 and the plane P2 and form a trough or base defined by a substantially planar portion 363. Both the raised areas 351 and the recesses 353 are located side by side above the plane P2 of the second material 337.

The topsheet 326 may comprise substantially planar sections 369 located between pairs of adjacent raised areas 351, as shown in FIG. 22, i.e., between diagonally positioned raised areas 351-1 and 351-3. The substantially planar sections 369 may generally be positioned in a plane parallel to or in the same plane as plane P2.

The three-dimensional features, i.e., the raised areas 351 and recesses 353, may be disposed in any suitable density across the surface of the multi-layer material 300, 300'. The features may, for example, be present in a density of: from about 20 to about 200 features; from about 30 to about 150 features, from about 40 to about 130 features; from about 60 to about 100 features, in an area of 10 cm$^2$.

A void 359 may be defined between each raised area 351 and a corresponding substantially planar area 337A of a wearer-facing surface of an adjacent layer of material. In the FIG. 23 aspect, the planar areas 337A may form part of a wearer-facing surface of a substantially planar region of the second material 337. For example, the voids 359 may be defined in the raised areas 351 intermediate a garment-facing surface of the topsheet 326 and the wearer-facing surface of the substantially planar region of the second material 337, as shown in the aspect illustrated in FIGS. 23-27. The topsheet 326 may be free from contact with the second material 337 in the raised areas 351. The topsheet 326 may be joined to the second material 337 in the recesses 353, e.g., at one or more points along the substantially planar portions 363 of the recesses 353. In some aspects, the topsheet 326 may also be joined to the second material 337 at the generally planar sections 369, see FIG. 22. The voids 359 under the topsheet 326 may help penetration of BM/liquid through the topsheet 326 and provide void volume for BM or other bodily fluid retention so that BM or other bodily fluids may pass to the second material 337 and be absorbed into the second material 337 and the absorbent core 330 or may be at least partially dewatered by the second material 337 and the absorbent core 330.

A width or circumference of each raised area 351 may be greatest at a point nearest the plane P2, as described above with respect to the raised areas 251 of FIG. 17A.

One or more apertures may be formed in the topsheet 326, the second material 337, and/or one or more other components of the absorbent article 100'. The apertures may extend completely or partially through a thickness of the respective component(s). As shown in the aspects depicted in FIGS. 22-27, the substantially planar outer portions 361 of the raised areas 351 may be continuous, i.e., free of any apertures.

An aperture 377, 377' may be formed in a central location of the planar portion or base 363, e.g., at a lower center point of the base central location, of each of at least a majority of the recesses 353. The apertures 377, 377' may extend through the topsheet 326 and fully or partially through the second material 337. In some aspects, one or both of the topsheet 326 or the second material 337 may comprise one respective layer of material, and in other aspects, one of both of the topsheet 326 or the second material 337 may each comprise two or more layers of material.

Figure 24:
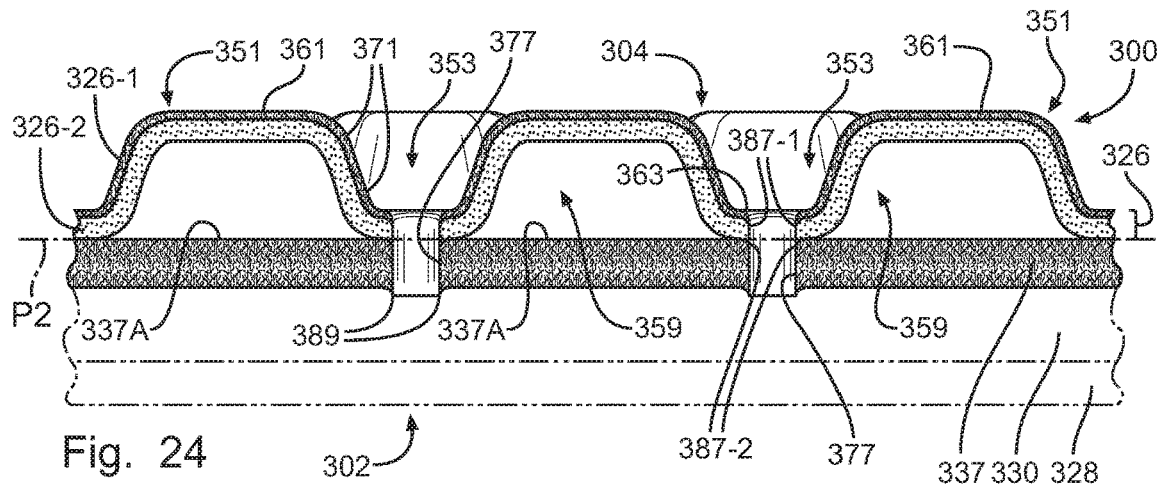
FIGS. 24-27 are cross-sectional views, similar to FIG. 23, of alternative aspects of an example absorbent article comprising a multi-layer material having a plurality of three-dimensional features in the form of raised areas and recesses, in which the recesses comprise apertures.

In the aspects depicted in FIGS. 23 and 24, the topsheet 326 comprises two or more layers of material, e.g., a first layer 326-1 and a second layer 326-2, and the second material 337 comprises one layer of material. Each aperture 377 may extend completely through a thickness of both layers 326-1, 326-2 of the topsheet 326 and the second material 337. The first and second layers 326-1, 326-2 of the topsheet 326 may both comprise a nonwoven material as described herein. In FIG. 23, the first layer 326-1 of the topsheet 326, e.g., the layer on the wearer-facing surface of the topsheet 326, may comprise a cotton-containing material, and the second layer 326-2 of the topsheet 326 may comprise a non-cotton material, in which the cotton-containing material may comprise a hydrophilic material mixed with hydrophobic cotton. In FIG. 24, the first layer 326-1 of the topsheet 326 may comprise a non-cotton material, and the second layer 326-2 of the topsheet 326, e.g., the layer on the garment-facing surface of the topsheet 326, may comprise a cotton-containing material, in which the cotton-containing material may be hydrophobic. In some aspects, the first and second layer 326-1, 326-2 of the topsheet 326 may both comprise a cotton-containing material or a non-cotton containing material.

In other aspects, the first layer 326-1 of the topsheet 326 may less hydrophilic than the second layer 326-2, which may define a hydrophilicity gradient as described above that keeps fluid and BM away from the skin of the wearer. The second material 337 could be even more hydrophilic than the second layer 326-2. In some particular aspects, the less hydrophilic first layer 326-1 may have a smaller denier than the more hydrophilic second layer 326-2, which may result in the first layer 326-1 having a higher degree of tactile softness and the second layer 326-2 being more permeable to fluids and BM. The second material 337 could be even more hydrophilic and permeable than the second layer 326-2. The FIG. 24 aspect may have the additional benefit that the cotton-containing second layer 326-2 of the topsheet 326 may be sandwiched between the first layer 326-1 of the topsheet 326 and the second material 337, which reduces the amount of cotton fiber and dust buildup on the machinery during the aperturing process and also minimizes the amount of cotton fibers that reach the skin of the wearer.

Figure 25:
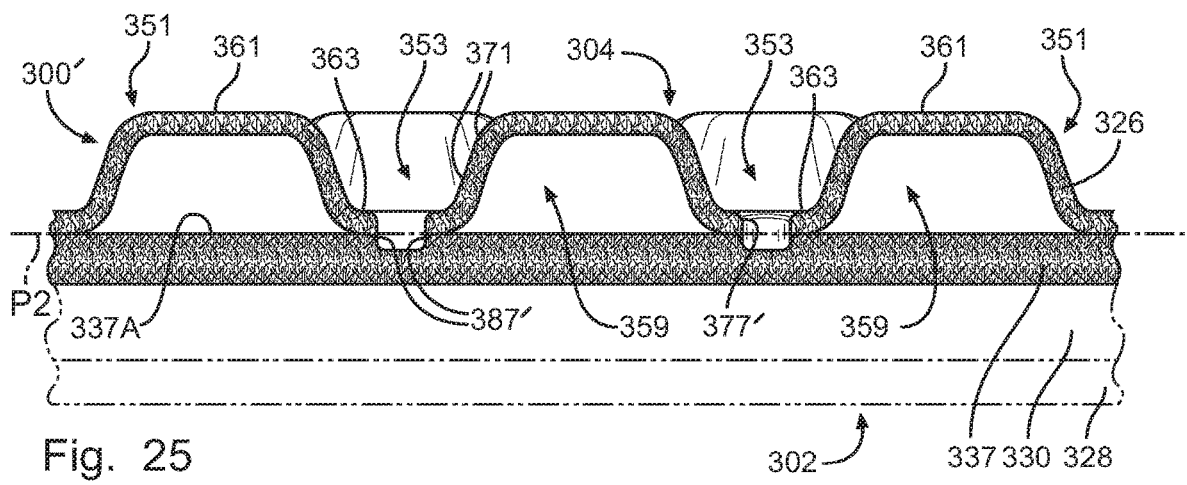
Figure 26:
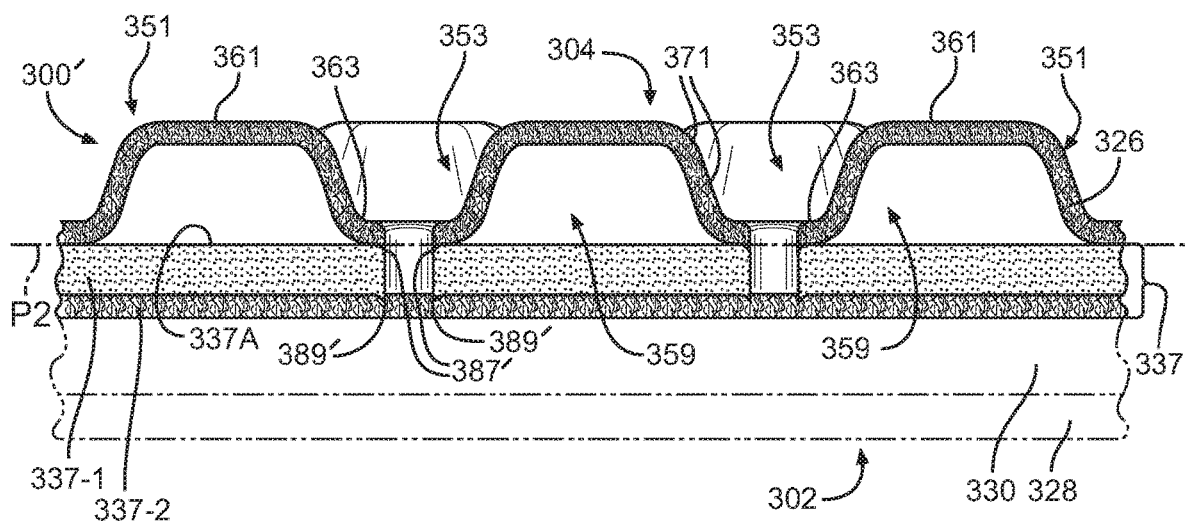
Figure 27:
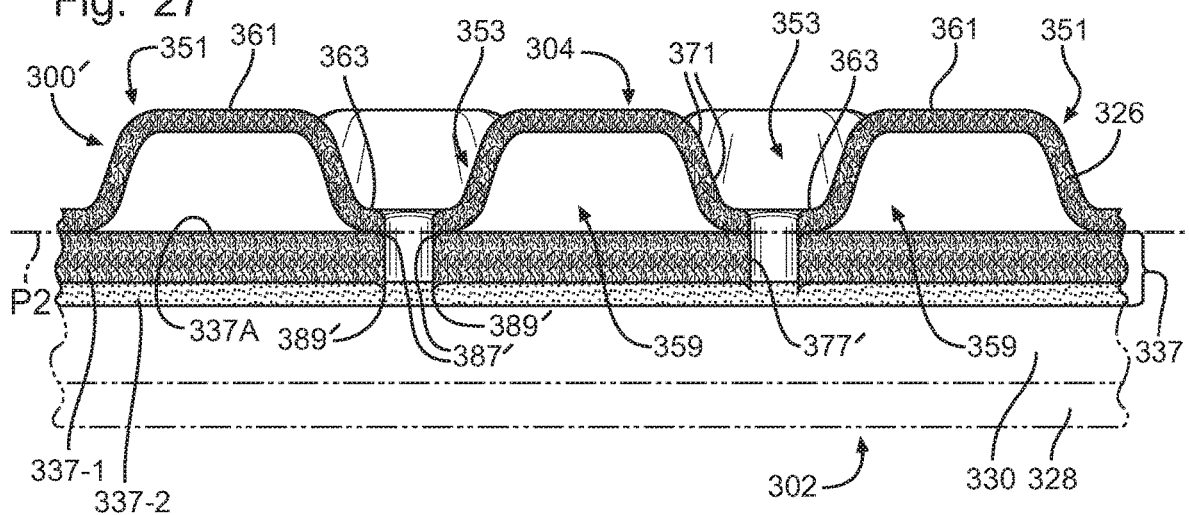

In the aspects depicted in FIGS. 25-27, the topsheet 326 comprises a single layer of material, and the second material 337 comprises one or more layers of material. The apertures 377' formed in at least a portion of the recesses 353 extend completely through the topsheet 326 but extend only partially through the second material 337 (within normal manufacturing tolerances). In the FIG. 25 aspect, the second material 337 may comprise a single layer of material, e.g., a nonwoven material as described herein, in which the apertures 377' extend completely through the topsheet 326 and only partially through the single-layer second material 337. In other aspects such as those depicted in FIGS. 26 and 27, the second material 337 comprises two or more layers of material, e.g., a first layer 337-1 and a second layer 337-2, in which the apertures 377' extend completely through the topsheet 326 and the first layer 337-1 of the second material 337 but do not extend through the second layer 337-2 of the second material 337.

The first and second layers 337-1, 337-2 of the second material 337 may both comprise a nonwoven material as described herein. In FIG. 26, the first layer 337-1 of the second material 337 may comprise a cotton-containing material, and the second layer 337-2 of the second material 337 may comprise a non-cotton material. In FIG. 27, the first layer 337-1 of the second material 337 may comprise a non-cotton material, and the second layer 337-2 of the second material 337 may comprise a cotton-containing material. In some aspects, the first and second layer 337-1, 337-2 of the second material 337 may both comprise a cotton-containing material or a non-cotton material. The benefits of the first and second layers 337-1, 337-2 of the second material 337 may be substantially similar to those described above with respect to the two layers 326-1, 326-2 of the topsheet 326 in FIGS. 23 and 24.

In other aspects, the recesses 353 may each comprise two or more apertures. In further aspects, one or more additional apertures may be formed under the raised areas 351 in a corresponding substantially planar area 337A of the second material 337 (not shown in FIGS. 23-27, but similar to the apertures 279 depicted in FIGS. 17A, 18, and 19). The apertures formed under the raised areas 351 may extend completely or partially through a thickness of the second material 337. The apertures 377, 377' may be shaped and sized in the same manner as described above with regards to the apertures 277, 277' of the aspect illustrated in FIGS. 16 and 17A-17C. Any suitable process may be utilized to form the apertures 377, 377', as described above with regards to the apertures 277, 277' of the aspect illustrated in FIGS. 16 and 17A-17C. The sidewalls 371 defining the raised areas 351 and the recesses 353 may be continuous and may be free of any additional apertures, as shown in FIGS. 23-27. The benefits of the multi-layer material 300, 300' in the examples of FIGS. 22-27 may be substantially similar to those described above with respect to the multi-layer material 200, 200' of the examples of FIGS. 16, 17A-C, and 18-21.

With reference to FIGS. 23-27, the recess bases 363 in which the apertures 377, 377' are formed may comprise small pieces or flaps of material that remain attached to circumferential edges of the apertures 377, 377' following manufacture of the absorbent article 100'. These flaps may comprise substantially the same structure and may provide substantially the same advantages as discussed above with regards to the flaps of the example absorbent article 100 depicted in FIGS. 16, 17A, and 18-21. As shown in FIGS. 23 and 24, the topsheet 326 may comprise two or more layers, e.g., a first layer 326-1 and a second layer 326-1, and the apertures 377 formed in the recesses 353 may comprise flaps 387-1, 387-2 respectively formed from portions of the first and second layers 326-1, 326-2 of the topsheet 326 and extending at least partially into an adjacent layer of material. In other aspects, the apertures 377' may comprise flaps 387' formed from a single-layer topsheet 326, see FIGS. 25-27. The apertures 377, 377' depicted in FIGS. 23-27 may further comprise flaps 389, 389', comprising portions of the second material 337.

In all aspects, the portion of the multi-layer material 200, 200', 300, 300' comprising the raised areas 251, 351 and recesses 253, 353 may be free of continuous ridges and continuous grooves. For example, as shown in FIGS. 16 and 22, each raised area 251, 351 may be discrete and not continuous with neighboring raised areas 251, 351. Each recess 253, 353 may be also discrete and not continuous with neighboring recesses 253, 353.

The raised areas 251, 351 may form more than 50% of a total area of the topsheet 226, 326 in some aspects, as shown in FIGS. 16, 17A, and 18-27. In other aspects, the raised areas 251, 351 may comprise less than 50% of the total area of the topsheet 226, 326.

Examples/Combinations

A. An absorbent article comprising:
    a liquid permeable nonwoven topsheet;
    a nonwoven second material, wherein the second material is a separate material from the topsheet;
    a liquid impermeable backsheet;
    an absorbent core positioned at least partially intermediate the second material and the liquid impermeable backsheet;
    wherein the second material is positioned intermediate the liquid permeable topsheet and the absorbent core;
    wherein the topsheet comprises a plurality of recesses and a plurality of raised areas;
    wherein the second material is generally planar;
    wherein portions of the recesses are joined to portions of the second material;
    wherein a first aperture is formed in a substantially central location of at least a majority of the raised areas, and wherein the first aperture extends through only the topsheet;
    wherein the recesses each comprise a base positioned most distal from the substantially central locations of the raised areas;
    wherein a second aperture is formed in at least a majority of the bases of the recesses, and wherein the second aperture extends through the topsheet and at least partially through the second material;
    wherein sections of the recesses and the raised areas intermediate the first apertures and the second apertures are free of any apertures; and
    wherein a void is defined intermediate a garment-facing surface of the topsheet and a wearer-facing surface of the second material in the raised areas.
B. The absorbent article of Paragraph A, wherein the second material comprises an acquisition material.
C. The absorbent article of Paragraph A or B, wherein the topsheet is free of continuous ridges and continuous grooves.
D. The absorbent article of any one of Paragraphs A-C, wherein the topsheet is free from contact with the second material in the raised areas.
E. The absorbent article of any one of Paragraphs A-D, wherein the topsheet is hydrophobic, and wherein the second material is hydrophilic.
F. The absorbent article of any one of Paragraphs A-D, wherein the topsheet is more hydrophobic than the second material.
G. The absorbent article of any one of Paragraphs A-D, wherein the topsheet is less hydrophilic than the second material.
H. The absorbent article of any one of Paragraphs A-G, wherein the first apertures are in fluid communication with the voids.
I. The absorbent article of any one of Paragraphs A-H, wherein the first apertures and the second apertures are cylindrical or ovate.
J. The absorbent article of any one of Paragraphs A-I, wherein the first apertures and the second apertures do not form conical shapes.
K. The absorbent article of any one of Paragraphs A-J, wherein the first apertures and the second apertures have a major axis that is less than 4 mm, preferably less than 3 mm.

L. The absorbent article of any one of Paragraphs A-K, wherein the raised areas form more than 50% of a total area of the topsheet.

M. The absorbent article of any one of Paragraphs A-L, wherein the raised areas are discrete.

N. The absorbent article of any one of Paragraphs A-M, wherein a third aperture is defined in the second material under each of at least a majority of the raised areas.

O. The absorbent article of any one of Paragraphs A-N, wherein the second material defines a plurality of third apertures under each of at least a majority of the raised areas.

P. The absorbent article of any one of Paragraphs A-O, wherein the topsheet or the second material comprises a cotton-containing layer and a non-cotton containing layer.

Q. The absorbent article of Paragraph P, wherein the second material comprises the cotton containing layer and the non-cotton containing layer, and wherein the second aperture extends only through the cotton-containing layer and not the non-cotton containing layer.

R. The absorbent article of Paragraph P, wherein the second material comprises the cotton containing layer and the non-cotton containing layer, and wherein the second aperture extends only through the non-cotton containing layer and not the cotton-containing layer.

S. The absorbent article of any one of Paragraphs P-R, wherein the cotton-containing layer is hydrophobic.

T. The absorbent article of any one of Paragraphs A-S, wherein the second aperture extends fully through the second material.

U. The absorbent article of any one of Paragraphs A-S, wherein the second aperture extends fully through the topsheet and only partially through the second material.

V. The absorbent article of any one of Paragraphs A-U, wherein the second material has a higher denier per filament than a denier per filament of the topsheet.

W. The absorbent article of any one of Paragraphs A-V, wherein one or more of the raised areas comprise a substantially planar outer portion.

X. The absorbent article of any one of Paragraphs A-W, wherein the opacity of the topsheet is greater than about 40% and the opacity of the second material is greater than about 45%.

Test Methods

Unless indicated otherwise, all tests described herein are made with samples conditioned at least 24 hours at 23° C.±2° C. and 50%±10% Relative Humidity (RH).

Raised Area Factor Test Method.

1) General Information

The Raised Area Factor of the three-dimensional protrusions, e.g., the raised areas described herein, of the topsheet/second material laminate of an absorbent article are measured using a GFM Primos Optical Profiler instrument commercially available from GFMesstechnik GmbH, Warthestraße 21, D14513 Teltow/Berlin, Germany. Alternative suitable non-touching surface topology profilers having similar principles of measurement and analysis, can also be used; here GFM Primos is exemplified.

The GFM Primos Optical Profiler instrument includes a compact optical measuring sensor based on a digital micro mirror projection, consisting of the following main components:

a) DMD projector with 800×600 direct digital controlled micro-mirrors
b) CCD camera with high resolution (640×480 pixels)
c) Projection optics adapted to a measuring area of at least 30×40 mm
d) Recording optics adapted to a measuring area of at least 30×40 mm
e) A table tripod based on a small hard stone plate
f) A cold light source (an appropriate unit is the KL 1500 LCD, Schott North America, Inc., Southbridge, Mass.)
g) A measuring, control, and evaluation computer running ODSCAD 6.3 software Turn on the cold-light source. The settings on the cold-light source are set to provide a color temperature of at least 2800 K.

Turn on the computer, monitor, and open the image acquisition/analysis software. In the Primos Optical Profiler instrument, select "Start Measurement" icon from the ODSCAD 6.3 task bar and then click the "Live Image button".

The instrument is calibrated according to manufacturer's specifications using calibration plates for lateral (X-Y) and vertical (Z). Such Calibration is performed using a rigid solid plate of any non-shiny material having a length of 11 cm, a width of 8 cm and a height of 1 cm. This plate has a groove or machined channel having a rectangular cross-section, a length of 11 cm, a width of 6.000 mm and an exact depth of 2.940 mm. This groove is parallel to the plate length direction. After calibration, the instrument must be able to measure the width and depth dimensions of the groove to within ±0.004 mm.

2) The Raised Area Factor

The absorbent article comprising the topsheet/second material laminate with three-dimensional protrusions or raised areas, i.e., corresponding to the sample (conditioned at a temperature of 23° C.±2° C. and a relative humidity of 50%±10% for at least 24 hours) is laid down on a hard flat horizontal surface with the wearer-facing surface upward, i.e., the topsheet of the topsheet/second material laminate facing up.

Ensure that the sample is lying in planar configuration, without being stretched, with the topsheet/second material laminate uncovered. If the absorbent article features cuff and/or leg elastics, they may be carefully removed from the absorbent article by aid of scissors to eliminate any tension in the absorbent article. A nominal external pressure of 1.86 kPa (0.27 psi) is then applied to the sample. Such nominal external pressure is applied without interfering with the topology profile measurement. Such an external pressure is applied using a transparent, non-shining flat Plexiglas® plate 200 mm by 70 mm and appropriate thickness (approximately 5 mm) to achieve a weight of 83 g. The plate is gently placed on top of the sample, such that the center point of the Plexiglas® plate is at least 40 mm away from any folds, with the entire plate resting on the sample. A fold corresponds to a part of the absorbent article (e.g. the topsheet/second material laminate) where the absorbent article has been folded for packaging purposes.

Two 50 mm×70 mm metal weights each having a mass of 1200 g (approximate thickness of 43 mm) are gently placed on the Plexiglas® plate such that a 70 mm edge of each metal weight is aligned with the 70 mm edges of the Plexiglas® plate. A metal frame having external dimensions of 70 mm×80 mm and interior dimensions of 42 mm×61 mm, and a total weight of 142 g (approximate thickness 6 mm), is positioned in the center of the Plexiglas® plate between the two end weights with the longest sides of the frame aligned with the longest sides of the plate.

If the topsheet/second material laminate is smaller than 70×200 mm, or if a large enough area without a fold is not present, or if an area of interest is close to the edges of the topsheet/second material laminate and cannot be analyzed with the Plexiglas® and weights settings described above, then the X-Y dimensions of the Plexiglas® plate and the added metal weights will be adjusted to reach a nominal external pressure of 1.86 kPa (0.27 psi) while maintaining a minimum 30×40 mm field of view. At least 10 complete three-dimensional protrusions on the sample should be captured in the field of view of 30 mm×40 mm.

Position the projection head to be normal to the sample surface (i.e. the topsheet of the topsheet/second material laminate).

Adjust the distance between the sample and the projection head for best focus.

In the Primos Optical Profiler instrument, turn on the button "Pattern" to make a red cross appear on the screen cross and a black cross appears on the sample.

Adjust the focus control until the black cross is aligned with the red cross on the screen.

Adjust image brightness then capture a digitized image.

In the Primos Optical Profiler instrument, change the aperture on the lens through the hole in the side of the projector head and/or altering the camera "gain" setting on the screen.

When the illumination is optimum, the red circle at the bottom of the screen labeled "I.O." will turn green.

Click on the "Measure" button.

The topology of the upper surface of the topsheet/second material laminate sample is measured through the Plexiglas® plate over the entire field of view 30 mm×40 mm. It is important to keep the sample still during this time in order to avoid blurring of the captured image. The image should be captured within the 30 seconds following the placement of the Plexiglas® plate, metal weights, and frame on top of the specimen.

After the image has been captured, the X-Y-Z coordinates of every pixel of the 40 mm×30 mm field of view area are recorded. The X direction is the direction parallel to the longest edge of the rectangular field of view, the Y direction is the direction parallel to the shortest edge of the rectangular field of view. The Z direction is the direction perpendicular to the X-Y plane. The X-Y plane is horizontal. These data are smoothed and filtered using a polynomial filter (n=6), a median filter 11 pixels by 11 pixels, and a structure filter 81 pixels by 81 pixels. The polynomial filter (n=6) approximates the X-Y-Z coordinate surface with a polynomial of order 6 and returns the difference to the approximated polynomial. The median filter 11 pixels by 11 pixels divides the field of view (40 mm×30 mm) in X-Y squares of 11 pixels by 11 pixels. The Z coordinate of the pixel located at the center of a given 11 pixels by 11 pixels square will be replaced by the mean Z value of all the pixels of this given square. The structure filter 81 pixels by 81 pixels, removes the waviness of the structure and translates all the Z peak values belonging to the bottom surface of the Plexiglas® plate to a top X-Y plane.

A Reference Plane is then defined as the X-Y plane intercepting the surface topology profile of the entire field of view (i.e. 30 mm×40 mm), 100 microns below this top X-Y plane. Then the Material Area of the Reference Plane is determined. The Material Area is the area of the Reference Plane that is below the surface profile. The Raised area factor is then calculated as the ratio between the Material Area of the Reference Plane and the total field of view area (i.e. 30 mm×40 mm). In the Primos Optical Profiler instrument, to measure the Material Area of the Reference Plane (Z=−0.1 mm), click on the button "Evaluate". Then apply a pre-filtering routine including a polynomial filter (n=6), a median filter 11 by 11 and a structure filter (n=81) using the function "Filter".

Save the image to a computer file with ".omc" extension.

Click on "Evaluate" and "Void area evaluation".

Set the highest cutting plane to Z=0 and update the settings via clicking on "Calculate new". Once the highest cutting plane is set to Z=0, then enter Z=−0.1 mm as the height of the Reference Plane at which the Material area will be measured and update the settings clicking on "Update". The Material Area is then calculated.

The same above procedure set out in the Raised Area Factor is then performed on the topsheet/second material laminate with the garment-facing surface upward, i.e., the acquisition layer of the topsheet/second material laminate facing up, in which the 40 mm×30 mm field of view is located at the exact same X-Y position of the topsheet/second material laminate.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any aspect disclosed or claimed herein or that it alone, or in any combination with any other reference or references, teaches, suggests or discloses any such aspect. Further, to the extent that any meaning or definition of a term in this document conflicts with any meaning or definition of the same term in a document incorporated by reference, the meaning or definition assigned to that term in this document shall govern.

While particular aspects of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
  a liquid permeable nonwoven topsheet;
  a nonwoven second material, wherein the second material is a separate material from the topsheet;
  a liquid impermeable backsheet;
  an absorbent core positioned at least partially intermediate the second material and the liquid impermeable backsheet;
  wherein the second material is positioned intermediate the liquid permeable topsheet and the absorbent core;
  wherein the topsheet comprises a plurality of recesses and a plurality of raised areas;
  wherein the second material is generally planar;
  wherein portions of the recesses are joined to portions of the second material;
  wherein a first aperture is formed in a substantially central location of at least a majority of the raised areas, and wherein the first aperture extends through only the topsheet;

wherein the recesses each comprise a base positioned most distal from the substantially central locations of the raised areas;

wherein a second aperture is formed in at least a majority of the bases of the recesses, and wherein the second aperture extends through the topsheet and at least partially through the second material;

wherein sections of the recesses and the raised areas intermediate the first apertures and the second apertures are free of any apertures;

wherein a void is defined intermediate a garment-facing surface of the topsheet and a wearer-facing surface of the second material in the raised areas; and wherein a third aperture is defined in the second material under each of at least a majority of the raised areas.

2. The absorbent article of claim 1, wherein the second material comprises an acquisition material.

3. The absorbent article of claim 1, wherein the topsheet is free of continuous ridges and continuous grooves.

4. The absorbent article of claim 1, wherein the topsheet is free from contact with the second material in the raised areas.

5. The absorbent article of claim 1, wherein the topsheet is hydrophobic, and wherein the second material is hydrophilic.

6. The absorbent article of claim 1, wherein the topsheet is more hydrophobic than the second material.

7. The absorbent article of claim 1, wherein the topsheet is less hydrophilic than the second material.

8. The absorbent article of claim 1, wherein the first apertures are in fluid communication with the voids.

9. The absorbent article of claim 1, wherein the first apertures and the second apertures are cylindrical or ovate.

10. The absorbent article of claim 1, wherein the first apertures and the second apertures do not form conical shapes.

11. The absorbent article of claim 1, wherein the first apertures and the second apertures have a major axis that is less than 4 mm.

12. The absorbent article of claim 1, wherein the raised areas form more than 50% of a total area of the topsheet.

13. The absorbent article of claim 1, wherein the raised areas are discrete.

14. The absorbent article of claim 1, wherein the second material defines a plurality of third apertures under each of at least a majority of the raised areas.

* * * * *